(12) United States Patent
Colliver et al.

(10) Patent No.: US 7,501,556 B2
(45) Date of Patent: Mar. 10, 2009

(54) NUTRITIONALLY ENHANCED PLANTS

(75) Inventors: Steven Peter Colliver, Sharnbrook (GB); Roy Thomas Dobb, Sharnbrook (GB); Hendrikus Theodorus Wilhelmus Maria van der Hijden, Vlaardingen (NL)

(73) Assignee: Unilever Patent Holdings B.V., Vlaardingen (NL)

( * ) Notice: Subject to any disclaimer, the term of this patent is extended or adjusted under 35 U.S.C. 154(b) by 392 days.

(21) Appl. No.: 10/505,145

(22) PCT Filed: Feb. 13, 2003

(86) PCT No.: PCT/EP03/01465

§ 371 (c)(1), (2), (4) Date: Apr. 8, 2005

(87) PCT Pub. No.: WO03/072790

PCT Pub. Date: Sep. 4, 2003

(65) Prior Publication Data

US 2005/0241014 A1    Oct. 27, 2005

(30) Foreign Application Priority Data

Feb. 28, 2002  (EP) ................. 02251404

(51) Int. Cl.
| | |
|---|---|
| *C12N 15/29* | (2006.01) |
| *C12N 15/52* | (2006.01) |
| *C12N 15/82* | (2006.01) |
| *A01H 5/00* | (2006.01) |

(52) U.S. Cl. ............ 800/282; 800/298; 800/305; 800/306; 800/308; 800/317.2; 800/317.3; 800/317.4

(58) Field of Classification Search .......... None
See application file for complete search history.

(56) References Cited

U.S. PATENT DOCUMENTS 7,038,113 B1 * 5/2006 Dixon et al. ............. 800/312

FOREIGN PATENT DOCUMENTS

| WO | WO 99/14351 | 3/1999 |
| WO | WO 00/44909 | 8/2000 |
| WO | WO 00/53771 | 9/2000 |

OTHER PUBLICATIONS

Yu, O. et al. in Plant physiology, Oct. 2000; vol. 124, pp. 781-793.*
Jez J. et al. Nature Structural Biology, 2000; vol. 7, No. 9, pp. 786-791.*
Jung et al., Identification and expression of isoflavone synthase, the key enzyme for biosynthesis of isoflavones in legumes, Nat. Biotechnol. (2000) 18:208-212.
Yu et al., Production of the Isoflavones Genistein and Daidzein in Non-Legume Dicot and Monocot Tissues, Plant Physiol. (2000) 124:781-793.

* cited by examiner

*Primary Examiner*—Russell Kallis
(74) *Attorney, Agent, or Firm*—Morgan, Lewis & Bockius LLP

(57) ABSTRACT

The present invention relates to the field of improving nutritional content and more particularly the isoflavone content in plants. The invention provides a process for increasing the content of the isoflavone daidzein in selected plants, novel plants produced by this process and products derivable therefrom.

31 Claims, 11 Drawing Sheets

Figure 5:
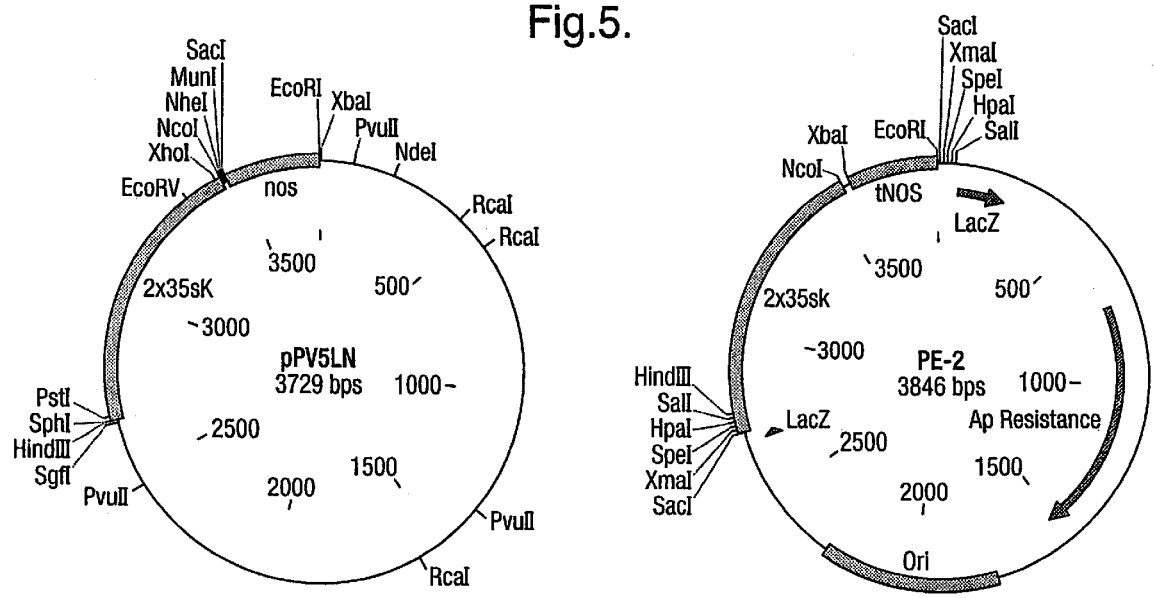

Pea Chalcone reductase DNA sequence (SEQ ID No. 1)

```
1    ATGGGTAGTG TTGAAATCCC AACAAAGGTG CTTACCAACA CATCTGCTCA AATTAAGATG
61   CCTGTTGTTG GAATGGGATC AGCACCTGAC TTCACATGCA AGAAAGACAC TAAAGAAGCA
121  ATCATCGAAG CCATCAAACA AGGTTACAGA CACTTTGATA CTGCTGCTGC TTATGGATCC
181  GAACAAGCTC TTGGTGAGGC TTTGAATGAG GCTATCAAC TTGGTCTTGT CACTAGAGAA
241  CAGCTTTTTG TTACTTCTAA ACTTTGGGTT ACTGAAAATC ATCCTCACCT TGTTCTTCCT
301  GCTCTACAAA AATCTCTCAA GACTCTTCAG TTGGATTACT TGGATTTGTA TTTGATTCAT
361  TGGCCACTTA GTTCTAGCC CGGAAAGTTT TCATTTCCAA TTGATGTGGC TGATCTATTG
421  CCATTTGATG TAAAAGGTGT GTGGGAATCC ATGGAAGAGG CTTTGAGACT TGGACTCACG
481  AAAGCTATTG GTGTCAGTAA CTTCTCTGTC AAGAAACTTC AAAAGCTACT ATCTGTTGCC
541  ACTGTTCTTC CTGCTGTTAA TCAAGTAGAG ATGAACCTTG CATGGCAACA AAAGAAGCTA
601  AGAGAATTTT GCAATGAAAA TGGAATAGTG TTGACTGCAT TTTCACCGTT GAGGAAAGGC
661  GCCAGCCGAG GAGCAAATGA GGTTATGGAG AATGATATGC TTAAACAGAT TGCAGATGCT
721  CATGGAAAGT CTATTGCACA AATTTCTCTG AGATGGTTAT ATGAACAAGG AATCACTTTT
781  GTTCCAAAGA GCTATGATAA GGAGAGAATG AGTCAAAATT TGAGAATCTT TGATTGGACA
841  CTGACAAAGG AGGATCATGA GAAAATTGAT CAAATTAAGC AGAATCGTTT GATCCCTGGA
901  CCAACCAAGC CAAGTCTCAA TGATCTTTGG GATGATGAAA TATAAG
```

Pea Chalcone reductase protein sequence (SEQ ID No. 2)

```
Met Gly Ser Val Glu Ile Pro Thr Lys Val Leu Thr Asn Thr Ser Ala Gln Ile Lys Met
Pro Val Val Gly Met Gly Ser Ala Pro Asp Phe Thr Cys Lys Lys Asp Thr Lys Glu Ala
Ile Ile Glu Ala Ile Lys Gln Gly Tyr Arg His Phe Asp Thr Ala Ala Ala Tyr Gly Ser
Glu Gln Ala Leu Gly Glu Ala Leu Asn Glu Ala Ile Gln Leu Gly Leu Val Thr Arg Glu
Gln Leu Phe Val Thr Ser Lys Leu Trp Val Thr Glu Asn His Pro His Leu Val Leu Pro
Ala Leu Gln Lys Ser Leu Lys Thr Leu Gln Leu Asp Tyr Leu Asp Leu Tyr Leu Ile His
Trp Pro Leu Ser Ser Gln Pro Gly Lys Phe Ser Phe Pro Ile Asp Val Ala Asp Leu Leu
Pro Phe Asp Val Lys Gly Val Trp Glu Ser Met Glu Glu Ala Leu Arg Leu Gly Leu Thr
Lys Ala Ile Gly Val Ser Asn Phe Ser Val Lys Lys Leu Gln Lys Leu Leu Ser Val Ala
Thr Val Leu Pro Ala Val Asn Gln Val Glu Met Asn Leu Ala Trp Gln Gln Lys Lys Leu
Arg Glu Phe Cys Asn Glu Asn Gly Ile Val Leu Thr Ala Phe Ser Pro Leu Arg Lys Gly
Ala Ser Arg Gly Ala Asn Glu Val Met Glu Asn Asp Met Leu Lys Gln Ile Ala Asp Ala
His Gly Lys Ser Ile Ala Gln Ile Ser Leu Arg Trp Leu Tyr Glu Gln Gly Ile Thr Phe
Val Pro Lys Ser Tyr Asp Lys Glu Arg Met Ser Gln Asn Leu Arg Ile Phe Asp Trp Thr
Leu Thr Lys Glu Asp His Glu Lys Ile Asp Gln Ile Lys Gln Asn Arg Leu Ile Pro Gly
Pro Thr Lys Pro Ser Leu Asn Asp Leu Trp Asp Asp Glu Ile
```

Fig. 1

REPLACEMENT SHEETS
Soy isoflavone synthase DNA sequence (SEQ ID No. 3)

```
   1   ATGGTGCTTG AACTTGCACT TGGTTTATTG GTTTTGGCTC TGTTTCTGCA CTTGCGTCCC
  61   ACACCCACTG CAAAATCAAA AGCACTTCGC CATCTCCCAA ACCCACCAAG CCCAAAGCCT
 121   CGTCTTCCCT TCATAGGACA CCTTCATCTC TTAAAAGACA AACTTCTCCA CTACGCACTC
 181   ATCGACCTCT CCAAAAAACA TGGTCCCTTA TTCTCTCTCT ACTTTGGCTC CATGCCAACC
 241   GTTGTTGCCT CCACACCAGA ATTGTTCAAG CTCTTCCTCC AAACGCACGA GGCAACTTCC
 301   TTCAACACAA GGTTCCAAAC CTCAGCCATA AGACGCCTCA CCTATGATAG CTCAGTGGCA
 361   ATGGTTCCCT TCGGGCCCTA CTGGAAGTTC GTGAGGAAGC TCATCATGAA CGACCTTCTC
 421   AACGCCACCA CTGTAAACAA GTTGAGGCCT TTGAGGACCC AACAGACGCG TAAGTTCCTT
 481   AGGGTTATGG CCCAAGGCGC AGAGGCACAG AAGCCCCTTG ACTTGACCGA GGAGCTTCTG
 541   AAATGGACCA ACAGCACCAT CTCCATGATG ATGCTCGGCG AGGCTGAGGA GATCAGAGAC
 601   ATCGCTCGCG AGGTTCTTAA GATCTTTGGC GAATACAGCC TCACTGACTT CATCTGGCCA
 661   TTGAAGCATC TCAAGGTTGG AAAGTATGAG AAGAGGATCG ACGACATCTT GAACAAGTTC
 721   GACCCTGTCG TTGAAAGGGT CATCAAGAAG CGCCGTGAGA TCGTGAGGAG GAGAAAGAAC
 781   GGAGAGGTTG TTGAGGGTGA GGTCAGCGGG GTTTTCCTTG ACACTTTGCT CGAGTTCGCT
 841   GAGGATGAGA CTATGGAGAT CAAAATCACC AAGGACCACA TCAAGGGTCT TGTTGTAGAC
 901   TTTTTCTCGG CAGGAACAGA CTCAACAGCG GTGGCAACAG AGTGGGCATT GGCAGAACTC
 961   ATCAACAATC CTAAGGTGTT GGAAAAGGCT CGTGAGGAGG TCTACAGTGT TGTGGGAAAG
1021   GACAGACTTG TGGACGAAGT TGACACTCAA AACCTTCCTT ACATTAGAGC AATCGTGAAG
1081   GAGACATTCC GCATGCACCC GCCACTCCCA GTGGTCAAAA GAAAGTGCAC AGAAGAGTGT
1141   GAGATTAATG GATATGTGAT CCCAGAGGGA GCATTGATTC TCTTCAATGT ATGGCAAGTA
1201   GGAAGAGACC CCAAATACTG GACAGACCA TCGGAGTTCC GTCCTGAGAG GTTCCTAGAG
1261   ACAGGGCTG AAGGGAAGC AGGGCCTCTT GATCTTAGGG ACAACATTT TCAACTTCTC
1321   CCATTTGGGT CTGGGAGGAG AATGTGCCCT GGAGTCAATC TGGCTACTTC GGGAATGGCA
1381   ACACTTCTTG CATCTCTTAT TCAGTGCTTC GACTTGCAAG TGCTGGGTCC ACAAGGACAG
1441   ATATTGAAGG GTGGTGACGC CAAAGTTAGC ATGGAAGAGA GAGCCGGCCT CACTGTTCCA
1501   AGGGCACATA GTCTTGTCTG TGTTCCACTT GCAAGGATCG GCGTTGCATC TAAACTCCTT
1561   TCTTAAG
```

Soy isoflavone synthase protein sequence (SEQ ID No. 4)

```
Met Val Leu Glu Leu Ala Leu Gly Leu Leu Val Leu Ala Leu Phe Leu His Leu
Arg Pro Thr Pro Thr Ala Lys Ser Lys Ala Leu Arg His Leu Pro Asn Pro Pro
Ser Pro Lys Pro Arg Leu Pro Phe Ile Gly His Leu His Leu Leu Lys Asp Lys
Leu Leu His Tyr Ala Leu Ile Asp Leu Ser Lys Lys His Gly Pro Leu Phe Ser
Leu Tyr Phe Gly Ser Met Pro Thr Val Val Ala Ser Thr Pro Glu Leu Phe Lys
Leu Phe Leu Gln Thr His Glu Ala Thr Ser Phe Asn Thr Arg Phe Gln Thr Ser
Ala Ile Arg Arg Leu Thr Tyr Asp Ser Ser Val Ala Met Val Pro Phe Gly Pro
Tyr Trp Lys Phe Val Arg Lys Leu Ile Met Asn Asp Leu Leu Asn Ala Thr Thr
Val Asn Lys Leu Arg Pro Leu Arg Thr Gln Thr Arg Lys Phe Leu Arg Val
Met Ala Gln Gly Ala Glu Ala Gln Lys Pro Leu Asp Leu Thr Glu Glu Leu Leu
Lys Trp Thr Asn Ser Thr Ile Ser Met Met Met Leu Gly Glu Ala Glu Glu Ile
Arg Asp Ile Ala Arg Glu Val Leu Lys Ile Phe Gly Glu Tyr Ser Leu Thr Asp
Phe Ile Trp Pro Leu Lys His Leu Lys Val Gly Lys Tyr Glu Lys Arg Ile Asp
Asp Ile Leu Asn Lys Phe Asp Pro Val Val Glu Arg Val Ile Lys Lys Arg Arg
Glu Ile Val Arg Arg Lys Asn Gly Glu Val Val Glu Gly Glu Val Ser Gly
Val Phe Leu Asp Thr Leu Leu Glu Phe Ala Glu Asp Glu Thr Met Glu Ile Lys
Ile Thr Lys Asp His Ile Lys Gly Leu Val Val Asp Phe Phe Ser Ala Gly Thr
Asp Ser Thr Ala Val Ala Thr Glu Trp Ala Leu Ala Glu Leu Ile Asn Asn Pro
Lys Val Leu Glu Lys Ala Arg Glu Val Tyr Ser Val Val Gly Lys Asp Arg
Leu Val Asp Glu Val Asp Thr Gln Asn Leu Pro Tyr Ile Arg Ala Ile Val Lys
Glu Thr Phe Arg Met His Pro Pro Leu Pro Val Val Lys Arg Lys Cys Thr Glu
Glu Cys Glu Ile Asn Gly Tyr Val Ile Pro Glu Gly Ala Leu Ile Leu Phe Asn
Val Trp Gln Val Gly Arg Asp Pro Lys Tyr Trp Asp Arg Pro Ser Glu Phe Arg
Pro Glu Arg Phe Leu Glu Thr Gly Ala Glu Gly Glu Ala Gly Pro Leu Asp Leu
Arg Gly Gln His Phe Gln Leu Leu Pro Phe Gly Ser Gly Arg Arg Met Cys Pro
Gly Val Asn Leu Ala Thr Ser Gly Met Ala Thr Leu Leu Ala Ser Leu Ile Gln
Cys Phe Asp Leu Gln Val Leu Gly Pro Gln Gly Gln Ile Leu Lys Gly Gly Asp
Ala Lys Val Ser Met Glu Glu Arg Ala Gly Leu Thr Val Pro Arg Ala His Ser
Leu Val Cys Val Pro Leu Ala Arg Ile Gly Val Ala Ser Lys Leu Leu Ser
```

Fig. 2

*Lotus corniculatus* chalcone isomerase DNA sequence (SEQ ID No. 5)

```
1    ATGGCTGCAT CCCTCACCCC AATCCAGGTC GAGAACCTTC AATTTCCTGC GTCTGTCACC
61   TCTCCAGCCA CCGCCAAGTC TTATTTCCTC GGTGGTGCAG GGGAGAGAGG GTTGACGATT
121  GAGGGGAAGT TCATAAAATT CACTGGCATA GGAGTGTATT TGGAAGATAC AGCAGTGGAT
181  TCACTCGCCA CCAAGTGGAA GGGTAAGAGT TCACAAGAGC TGCAGGACTC CCTTGACTTC
241  TTCAGAGACA TCATTTCAAG TCCCTCTGAG AAGTTAATTC GAGGGTCCAA GCTGAGGCCA
301  TTGAGTGGCG TGGAGTATTC AAGAAAGGTG ATGGAGAATT GTGTGGCACA CATGAAGTCT
361  GCTGGAACTT ATGGTGAAGC AGAGGCCACA GCCATTGAAA AATTTGCAGA AGCCTTCAGG
421  AAGGTGGATT TTCCACCAGG TTCCTCTGTT TTCTACCGAC AATCAACAGA TGGAAAATTA
481  GGGCTTAGTT TCTCTTTGGA TGACACGATA CCAGAAGAAG AGGCTGTAGT TATAGAGAAC
541  AAGGCACTCT CAGAGGCAGT GTTAGAGACC ATGATTGGCG AGCATGCTGT TTCCCCTGAT
601  TTGAAGCGTT GTTTGGCTGA AAGGTTGCCT ATTGTGATGA ACCAGGGTCT TCTCCTCACT
661  GGAAACTGAT
```

*Lotus corniculatus* chalcone isomerase protein (SEQ ID No. 6)

```
Met Ala Ala Ser Leu Thr Pro Ile Gln Val Glu Asn Leu Gln Phe Pro Ala Ser
Val Thr Ser Pro Ala Thr Ala Lys Ser Tyr Phe Leu Gly Gly Ala Gly Glu Arg
Gly Leu Thr Ile Glu Gly Lys Phe Ile Lys Phe Thr Gly Ile Gly Val Tyr Leu
Glu Asp Thr Ala Val Asp Ser Leu Ala Thr Lys Trp Lys Gly Lys Ser Ser Gln
Glu Leu Gln Asp Ser Leu Asp Phe Phe Arg Asp Ile Ile Ser Ser Pro Ser Glu
Lys Leu Ile Arg Gly Ser Lys Leu Arg Pro Leu Ser Gly Val Glu Tyr Ser Arg
Lys Val Met Glu Asn Cys Val Ala His Met Lys Ser Ala Gly Thr Tyr Gly Glu
Ala Glu Ala Thr Ala Ile Glu Lys Phe Ala Glu Ala Phe Arg Lys Val Asp Phe
Pro Pro Gly Ser Ser Val Phe Tyr Arg Gln Ser Thr Asp Gly Lys Leu Gly Leu
Ser Phe Ser Leu Asp Asp Thr Ile Pro Glu Glu Glu Ala Val Val Ile Glu Asn
Lys Ala Leu Ser Glu Ala Val Leu Glu Thr Met Ile Gly Glu His Ala Val Ser
Pro Asp Leu Lys Arg Cys Leu Ala Glu Arg Leu Pro Ile Val Met Asn Gln Gly
Leu Leu Leu Thr Gly Asn
```

Fig. 3

| ID No. | Primer | Primer Sequence (5' to 3') |
|---|---|---|
| 13 | GPTV1 | Ttgtccagatagcccagtagctg |
| 14 | GPTV2 | Cgacaatctgatcatgagcggag |
| 15 | 30035S | Cgcaagacccttcctctatataag |
| 16 | Gus2 | Gcatcacgcagttcaacgctg |
| 17 | 152 | Ggaaacagctatgaccatgattac |
| 18 | 160 | Aaggatccgtcgacatc |
| 19 | 167 | Agtcccccatggtacgtcctgtagaaacc |
| 20 | 168 | Cgttttcgtcggtaatcaccattcc |
| 21 | 191 | Tttcccagtcacgacgttgt |
| 22 | 198 | Gacatcgataatacgac |
| 23 | 248 | Tgctacctctagagaatttccccg |
| 24 | 321 | ctaagcccc/taag/tattccatcaggtgatt |
| 25 | 322 | ccaggtggaaaatta/cacat/gt/gcttgaaa/gagc |
| 26 | 323 | tttgaaaagt/ctaat/aa/cgagggtca/gaag |
| 27 | 324 | tactcaaggaaggtt/gatggag/aactgt/cgtgg |
| 28 | 329 | cgcgagctcatgtaccccgggatttccactagtttaagggttaactacatggtcgacgtacata |
| 29 | 330 | agcttatgtacgtcgaccatgtagttaatccttaaactagtggaaatcccggggtacatgagctcgcgat |
| 30 | 331 | aattcgagctcatgtaccccgggatttccactagtttaagggttaactacatggtcgacg |
| 31 | 332 | ctagcgtcgaccatgtagttaaccottaaactagtggaaatcccggggtacatgagctcg |
| 32 | 333 | catggatgcgtagttaagcct |
| 33 | 334 | ctagaggcttacatacgcatc |
| 34 | 337 | Aattcatgtacgagctcaattccccgggataggcactagtgctgctgttaactacatggtcgacttattaa |
| 35 | 338 | Aggtttaataagtcgaccatgtagttaacagcagcactagtgcctatcccgggggaattgagctcgtacatg |
| 36 | 339 | Gaacaccatggtgcttgaacttgc |
| 37 | 340 | Tccagtagggcccgaagggaaccattgccac |
| 38 | 341 | Ccttcgggccctactggaag |
| 39 | 342 | Cagcgaactcgagcaaagtg |
| 40 | 343 | Cactttgctcgagttcgctgaggatgagactatggagatcaaaatcaccaaggaccacatcaagggtcttgttgtagac |
| 41 | 344 | atgacgagctagcttattaagaaaggag |
| 42 | 362 | ggtgtgtggggatccatggaagaggctttg |
| 43 | 363 | cctcggctcgcgccttttcctcaacggtgaaaatgcagtcaacac |
| 44 | 384 | caacaacccatgggtagtgttgaaatcccaacaaggtgcttacc |
| 45 | 385 | agcaactgctagcttatatttcatcatcccaaagatc |
| 46 | 386 | tagattgccatggctgcatccctcaccccaatccaggtcgag |
| 47 | 387 | aaactttgctagcttatcagtttccagtgaggagaagac |
| 48 | 398 | gcttgttcggatccataagcagc |
| 49 | 399 | tgcttatggatccgaacaagctcttggtgaggctttgaatg |
| 50 | 400 | cagccacatcaattggaaatg |
| 51 | 401 | tcatttccaattgatgtggctgatctattgccatttgatgtaaaggtgtgtgggaatccatggaagaggctttgaga |
| 52 | 402 | cacaagagctgcaggactcccttga |
| 53 | 403 | gggagtcctgcagctcttgtgaac |
| 54 | 624 | agctgcgatcgcaagcttggtaccgggaattctctaga |
| 55 | 625 | aatttctagagaatttcccggtaccaagcttgcttgcgatcgc |
| 56 | 626 | tcgacccatggcccgctagccaattggagct |
| 57 | 627 | ccaattggctagcgggccatggg |
| 58 | 640 | ccacccacgagggaacatcgtg |
| 59 | 641 | gaattcccatggtttacactcgaggtcctctccaaatga |

Fig. 4

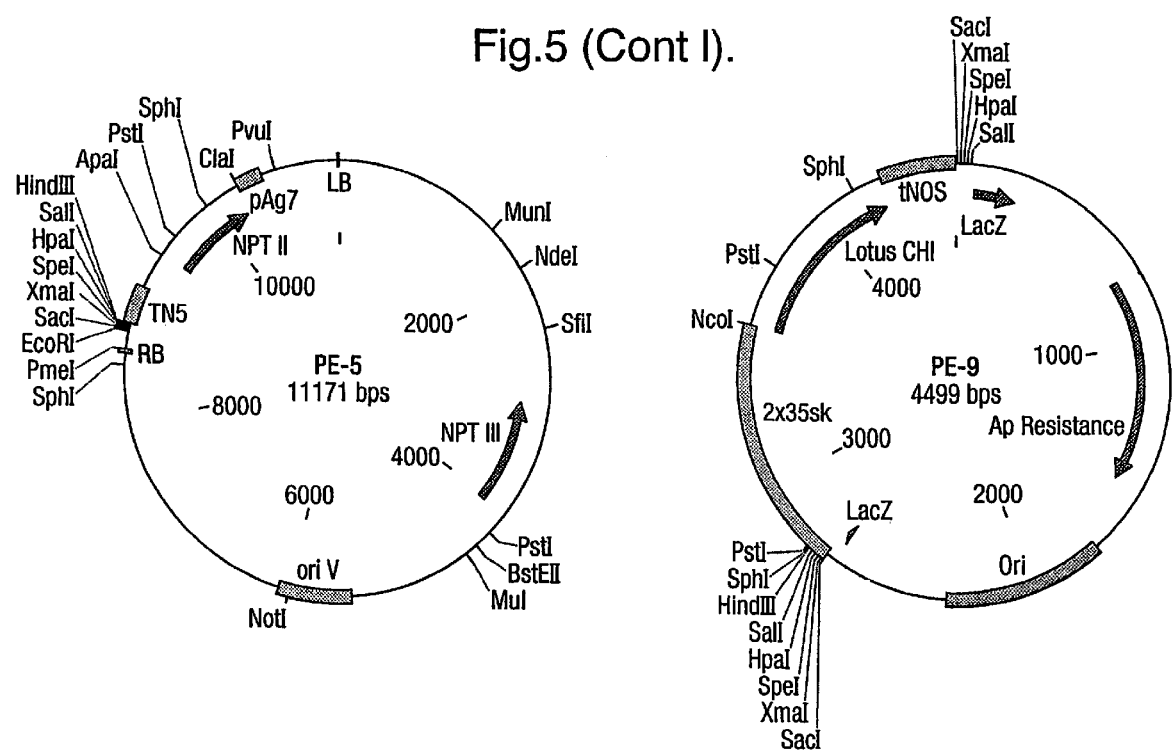
Fig.5 (Cont I).

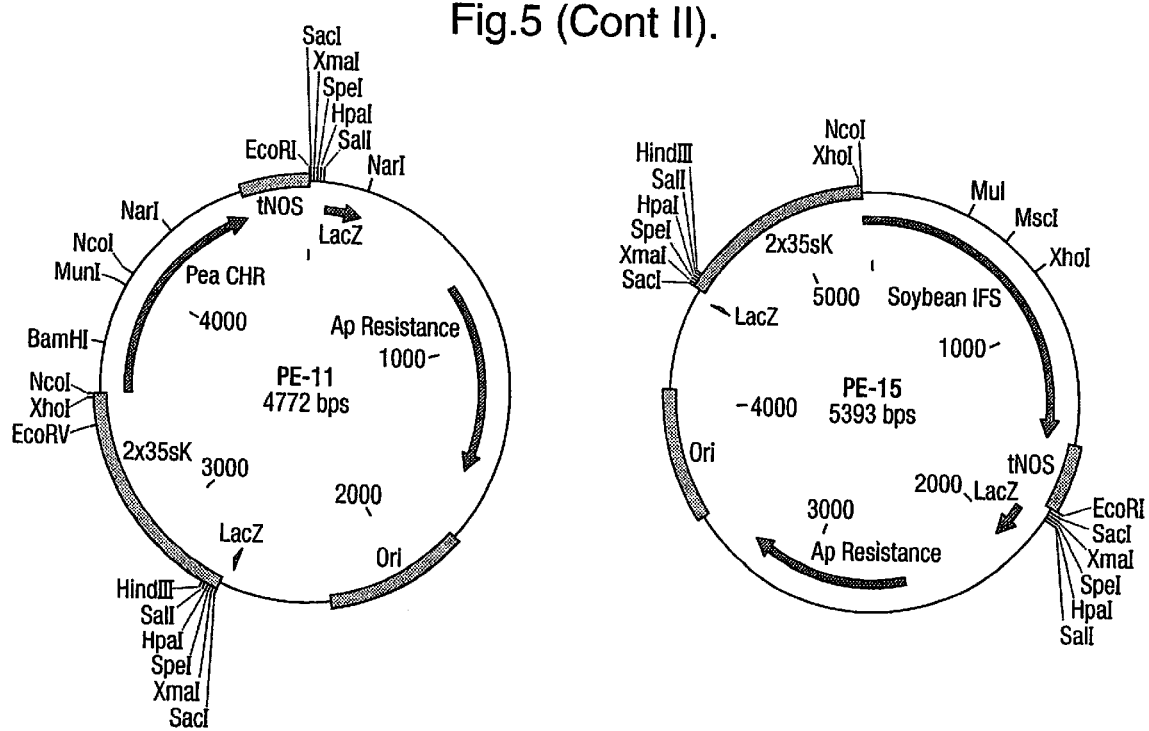
Fig.5 (Cont II).

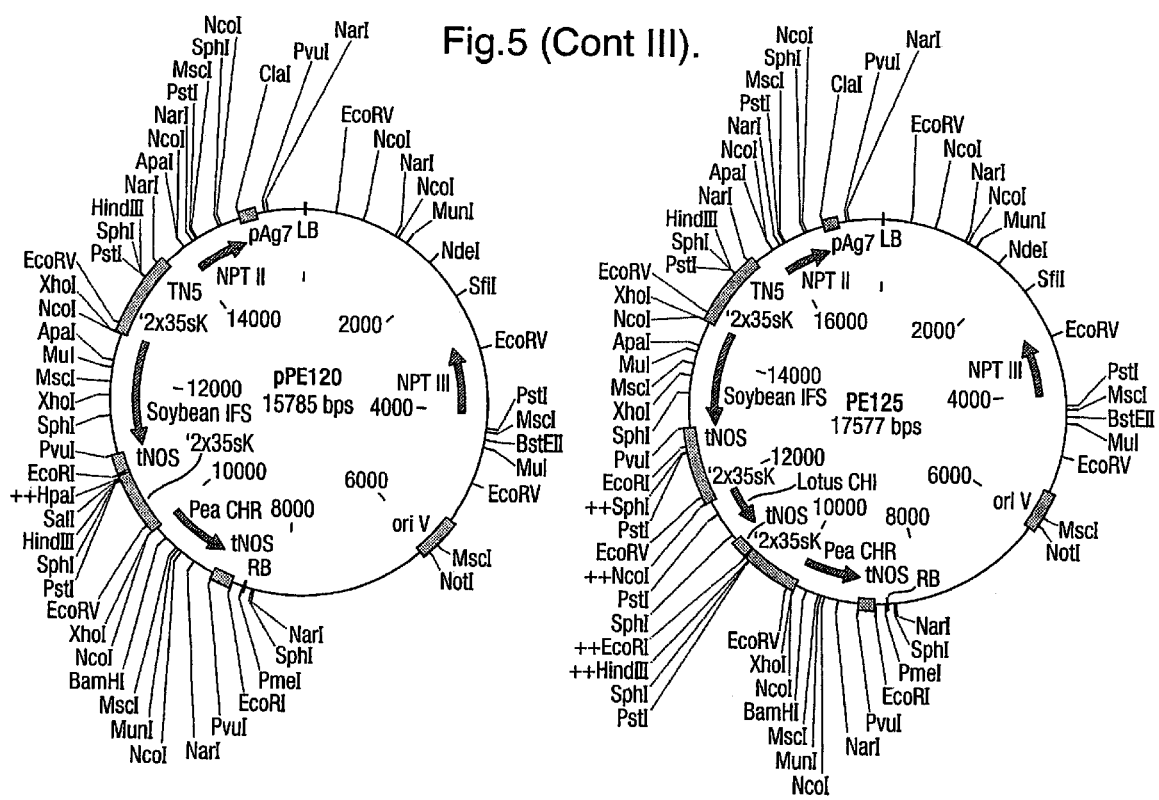

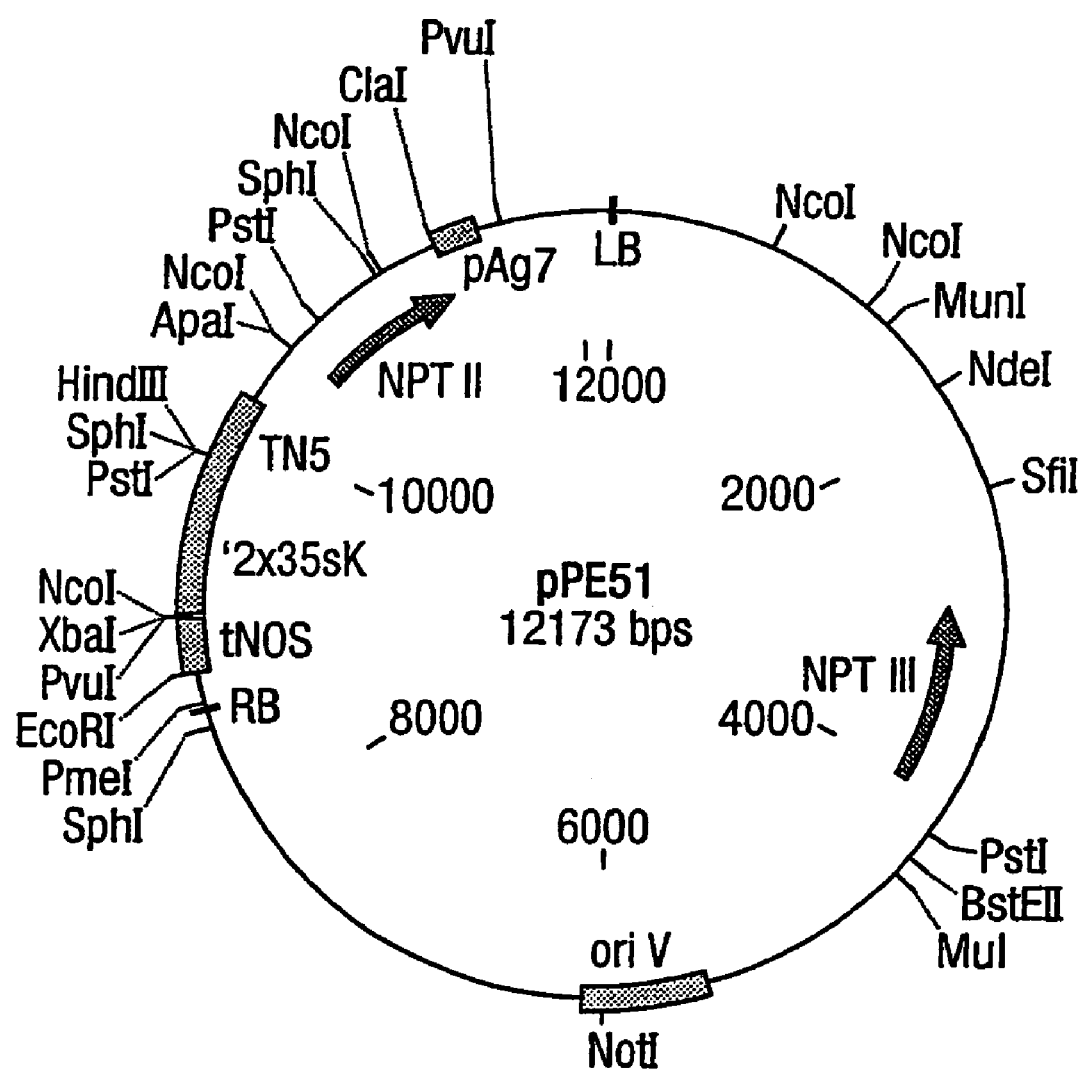
Fig.5 (Cont IIII).

NUTRITIONALLY ENHANCED PLANTS

The present application is a U.S. National Phase Application of International Application PCT/EP03/01465 (filed Feb. 13, 2003) which claims the benefit of European Patent Application EP 2251404.6 (filed Feb. 28, 2002) all of which are herein incorporated by reference in their entirety.

FIELD OF THE INVENTION

The present invention relates to the field of improving nutritional content in plants. More particularly the invention relates to the modification of selected plants to improve their content of oestrogenic compounds and to the plants and plant derived products obtainable therefrom.

BACKGROUND TO THE INVENTION

Isoflavones are a group of oestrogenic compounds which belong to the flavonoid class of plant secondary metabolites. These compounds are produced naturally in certain plants expressing the enzyme isoflavone synthase and in particular in leguminous plants. The presence of isoflavones is known to provide several advantages including the facilitation of anti-microbial plant defences and establishing bacterial or fungal symbioses within plants as well aiding nitrogen fixation in root nodules.

In addition to the advantages that are conferred to plants, the dietary presence of isoflavones is also believed to provide benefits to human health. For example, dietary isoflavones are believed to be effective at reducing the risk of cancer and cardiovascular disease.

At present, in the human diet the only sources of isoflavones are certain legumes, such as soybean or chickpea. Soy constitutes by far the major dietary source, however supplementation of food products with soy or soy-extracts may adversely affect the flavour profile. It would therefore be desirable to extend the range of plants or plant tissues capable of providing an effective source of isoflavones to the human diet and in particular a source which does not adversely affect the flavour profile of a product.

WO 00/53771 teaches that to form the isoflavone daidzein in transgenic plants that do not possess an isoflavonoid pathway and thus do not produce isoflavones in nature, it would be necessary to introduce therein three new genes, namely chalcone reductase (CHR) to co-act with chalcone synthase (CHS) to form 2',4,4'-trihydroxychalcone, a suitable chalcone isomerase (CHI) to convert 2',4,4'-trihydroxychalcone to liquiritigenin, and isoflavone synthase (IFS).

The applicants have now found that the approach disclosed in WO 00/53771 does not allow the formation of daidzein in respect of many plants. Furthermore the applicants believe that the transformation of the tomato plant as exemplified in example 3 of WO 00/53771 is most unlikely to produce tomatoes with increased levels of daidzein as purported to be achieved therein.

Studies carried out by Yu et al., (Production of isoflavones genistein and daidzein in non-legume dicot and monocot tissues. Plant Physiol. 2000 124:781-793) applied transcription factors C1 and R with the co-introduction of CHR and IFS into non-differentiated Black Mexican Sweet (BMS) maize cultures. This approach yielded only trace elements of daidzein in a single cell line.

The use of this single cell system in drawing any conclusions relating to enzymology and regulation of secondary metabolic pathways in differentiated tissues is recognised in the art as unreliable (Stafford H. A. (1990) CRC Press, Boca Raton, Fla. p. 225-239).

BMS maize cell cultures are undifferentiated and are not active in flavonol biosynthesis.

The objective technical problem to be solved by the present invention therefore relates to the need to provide novel plants which comprise significantly increased levels of daidzein and/or daidzein derivatives.

It has now been found that the solution to this problem lies in a process which selects a non-isoflavone producing plant or part thereof comprising both active anthocyanin and flavonol pathways and alters said plant to increase the enzyme activity of chalcone reductase and isoflavone synthase therein.

At the time of filing it was not known that the selection of a non-isoflavone producing plant comprising both active anthocyanin and flavonol biosynthetic pathways in combination with an increase in these specific enzyme activities could be used to provide plants with increased levels of daidzein and/or derivatives thereof.

Definition of Terms

A non-isoflavone producing plant is suitably defined by the absense of isoflavone synthase enzyme activity which renders the tissues of the plant unable to produce isoflavones. The absence of isoflavone synthase activity can be determined by achieving a negative result in a standard enzyme assay as disclosed in Jung et al., (Nature Biotech. Vol. 18 Feb. 2000 p. 208-212) incorporated herein by reference.

The term 'plant or part thereof' is used herein to refer to an entire plant or differentiated group of cells forming a part thereof. A part of a plant for the purpose of the invention may relate to leaves, stems, fruit, seeds, flowers, roots, tubers.

The expression 'increasing' is used in comparison to an equivalent unmodified plant or part thereof and may be on an absolute dry weight basis or in relative terms. Except for the modifications introduced by the process of the invention, this equivalent plant is genetically identical thereto.

Daidzein as used herein is taken to comprise 7,4'-dihydroxyisoflavone. Derivatives of daidzein are taken to comprise those molecules which result from the cellular biochemical modification of daidzein. Preferably a daidzein derivative is selected from the group comprising pterocarpans e.g. medicarpin, glyceollin, isoflavanones e.g. vestitone, rotenoids e.g. munduserone, isoflavans e.g. vestitol, α-methyldeoxybenzoins e.g. angolensin, 2-arylbenzofurans e.g. centrolobofuran, isoflavonols e.g. 7,2'-dihydroxy-4'-methoxy-isoflavonol, isoflav-3-enes e.g. haginin, 3-arylcoumarins e.g. glysyrin, coumestans e.g. coumestrol, coumaronochromones e.g. lupinalbin, coumaranochromene e.g. pachyrrhisomene.

Derivatives of daidzein may also result from one or more chemical processes selected from the group comprising methylation, glycosylation, prenylation and ether linkage.

A plant or part thereof that is active in anthocyanin biosynthesis has an active anthocyanin pathway and is taken to comprise a tissue which comprises mRNA encoding one or more enzymes selected from the group comprising dihydroflavonol reductase, proanthocyanidin synthase, and UDP-glucose:flavonoid-3-O-glucosyltransferase.

For the purpose of the present invention active anthocyanin biosynthesis may be determined in a plant tissue by a spectrophotometric test wherein absorbance of a hydrolysed plant extract at λvis-max 480-560 nm is indicative of an active anthocyanin pathway. Plant tissues are ground in liquid nitrogen and extracted with 80% (v/v) ethanol at 100 mg/700 µl for 30 min at room temperature (~22/C). Following extraction the cell debris is removed by filtration through a 0.45 µm Millex_HV filter unit (Millipore Corp, USA). The ethanol extract (360 µl) is mixed with 12M HCl (40 µl). The acidified ethanol extract is assayed by spectrophotometer and absorbance determined as $A_{\lambda vis\text{-}max\ 480\text{-}560nm}$, with the $A_{657}$ subtracted.

It is preferred that a plant or the part thereof that is active in anthocyanin biosynthesis contains more than 10 mg/kg fresh weight anthocyanin, more preferably at least 100 mg/kg, further preferred at least 1000 mg/kg and most preferred from 1000 to 10,000 mg/kg fresh weight. Suitably this is calculated from absorption values according the formula $C=A*MW*10^3*DF/(\epsilon*1)$ in which C refers to concentration, A refers to absorption (as defined above); MW is molecular weight; DF is dilution factor; $\epsilon$ is molar extinction coefficient (29,600 for cyanidin 3-glucoside the major anthocyanin in nature) and l is the path length.

A plant or part thereof which is active in flavonol biosynthesis has an active flavonol pathway and is taken to comprise any tissue which comprises mRNA encoding one or more enzymes selected from the group comprising chalcone synthase, chalcone isomerase, flavanone 3-hydroxylase, flavonol synthase.

For the purpose of the present invention whether a plant is active in flavonol biosynthesis may be determined by preparing a hydrolysed tissue extract and detection by HPLC analysis.

For extraction, tissues are harvested and flash frozen in liquid nitrogen before being stored at −80° C. The tissues are then ground to a fine powder to ensure a homogeneous mix. An aliquot from this mixture is then extracted for 30 min at room temperature (~22° C.) in 80% (v/v) ethanol at 100 mg/700 µl. Following extraction, the cell debris is removed by filtration through a 0.45 µm Millex-HV filter unit (Millipore Corp, USA). The filtrate is stored at −20° C. prior to HPLC analyses.

For hydrolysed extracts, 40 µl of 12M HCl is added to 360 µl from each tissue extract, before incubating at 90° C. for 40 min.

After hydrolysis, an aliquot from each extract is filtered through a 0.2 µm PTFE disposable filter (Whatman). The filtrate (20 µl) is injected into the HPLC system (HP1100, Agilent) via an autosampler maintained at 4° C. The analytical column (Prodigy Phenyl-3, 4.6×150 mm, particle size 5 µm, (Phenomenex) is held at 30° C. Detection is by diode array, monitoring at 262, 280, and 370 nm. Observed peaks are scanned from 210-550 nm to obtain spectra. Chemstation software (Rev. A.8.03) was used to control the system and collect and analyse data.

Absorbance spectra (corrected for baseline spectrum) and retention time of peaks are compared with those of commercially available flavonol standards to determine whether the plant tissue is active in flavonol biosynthesis.

It is preferred that a plant or the part thereof that is active in flavonol biosynthesis contains at least 10 mg/kg fresh weight of flavonol, preferably at least 100 mg/kg more preferred at least 1000 mg/kg, most preferred from 1000 to 10000 mg/kg.

A 'functional equivalent' nucleotide sequence is any sequence which encodes a protein which performs the same biological function.

According to another embodiment, a functionally equivalent nucleotide sequence shows at least 50% identity to the respective DNA sequence. More preferably a functionally equivalent DNA sequence shows at least 60%, more preferred at least 75%, even more preferred at least 80%, even more preferred at least 90%, most preferred 95-100% identity, to the respective DNA sequence (DNAStar MegAlign Software Version 4.05 and the Clustal algorithm set to default parameters).

According to a further preferred embodiment a functionally equivalent sequence shows not more than 5 base pairs difference to the respective DNA sequence, more preferred less than 3, e.g. only 1 or 2 base pairs different.

According to another embodiment a functionally equivalent sequence is capable of hybridising under low stringent (2×SSC, 0.1% SDS at 25° C. for 20 min) conditions to the respective sequence, more preferably a functionally equivalent sequence is capable of hybridising under medium stringent conditions (1×SSC, 0.1% SDS, 25° C. for 20 min), further preferred a functionally equivalent sequence is capable of hybridising under high stringent conditions (0.1× SSC, 0.1% SDS, 25° C. for 20 min).

Preferably an equivalent DNA sequence is capable of transcription and subsequent translation to an amino acid sequence showing at least 50% identity to the amino acid sequence encoded by the respective DNA sequence. More preferred, the amino acid sequence translated from an equivalent DNA sequence has at least 60%, more preferred at least 75%, even more preferred at least 80%, even more preferred at least 90%, most preferred 95-100% identity to the amino acid sequence encoded by the respective DNA sequence (DNAStar MegAlign Software Version 4.05 and the Clustal algorithm set to default parameters.)

BRIEF DESCRIPTION OF THE INVENTION

It has now been found that novel plants which comprise significantly increased levels of daidzein and/or daidzein derivatives may be provided by a plant or part thereof which has both active anthocyanin and flavonol pathways and has been genetically modified to increase the enzyme activity of CHR and IFS therein.

It is a therefore a first object of the invention to provide a genetically modified plant or part thereof comprising daidzein and/or derivatives thereof, wherein said plant or part thereof is active in flavonol and anthocyanin biosynthesis and comprises one or more nucleotide sequences encoding chalcone reductase and one or more nucleotide sequences encoding isoflavone synthase.

Particular advantage has been found to result from genetically modifying said plant to also increase the activity CHI, wherein production of daidzein in the tissues concerned showed a 90 fold increase over the modification to increase CHR and IFS activities alone. This additional benefit has been found to be dependent on the selection of a CHI isoform which is capable of catalysing the conversion of 4,2',4'-trihydroxychalcone to 7,4'-dihydroxyflavanone (liquiritigenin). Suitable CHI's are obtained from leguminous plants. At some 15 times (on a dry weight basis) the level of daidzein present in conventional soy this result represents a significant improvement to the art. This result is surprising and clearly demonstrates a synergy from a combined increase in these three enzyme activities where active anthocyanin and flavonol pathways are present in a plant.

A first embodiment of the invention therefore comprises a genetically modified plant or part thereof as described above, further comprising one or more nucleotide sequences encoding a chalcone isomerase capable of catalysing the conversion of 4,2',4'-trihydroxychalcone to 7,4'-dihydroxyflavanone.

A further embodiment of the invention comprises a genetically modified plant or part thereof as described above wherein said one or more nucleotides sequences comprise sequences according to sequence identification numbers 1 and 3, or functional equivalents thereof.

In the preferred instance where the synergistic advantage of an additional CHI increase is sought, the invention relates to an embodiment wherein said one or more nucleotides sequences comprises sequences according to sequence identification numbers 1, 3 and 5, or a functional equivalents thereof.

In a further embodiment the invention relates to a genetically modified plant or part thereof as described above wherein said plant or part thereof is selected from the group comprising, but not restricted to, tobacco, *Lactuca* sp., broccoli, asparagus, red cabbage, potato, spinach, rhubarb, red onion, shallot, aubergine, radish, Swiss chard, purple basil, watermelon and berries.

Plants or parts thereof modified in accordance with the invention to increase their content of daidzein and/or daidzein derivatives are particularly advantageous for providing health benefits associated with increased dietary uptake of isoflavones. Plants or parts thereof may therefore be used either in their natural state or prepared as a extract to treat disease states or induce health benefits as a preventative agent or by counter acting the ageing process.

A second object of the invention therefore provides an extract of a plant as described above wherein said extract comprises daidzein or derivatives thereof.

A third object of the invention provides an extract as described above for use as a medicament. In a preferred embodiment and extract according to the invention may be used in the treatment and/or prevention of one or more conditions selected from the group comprising, osteoporosis; cancer; menopausal and post menopausal symptoms comprising hot flushes, anxiety, depression, mood swings, night sweats, headaches, unrinary incontinence; pre-menstrual syndromes comprising fluid retention, cylical mastalgia, dysmenorrhoea; heart disease atherosclerosis; hypertension; coronary artery spasm; high cholesterol; Alzheimer's disease; impaired cognitive function; inflammatory diseases comprising inflammatory bowel disease, ulcerative colitis, Crohn's disease; and rheumatoid arthritis.

Cosmetic benefits may also be gained from the use of an extract as described above in the treatment and/or prevention of one or more conditions selected from the group comprising sunlight induced skin damage, skin wrinkling, loss of skin sensitivity, loss of skin firmness, acne, poor hair condition and baldness.

These medical and cosmetic benefits are also provided by the use of the genetically modified plants or parts thereof according to the invention. Uptake of the daidzein and/or its derivative may be via oral or topical applications.

For convenient dietary uptake of increased amounts of isoflavones a plant or part thereof according to the invention may suitably be incorporated into a food product or nutritional supplement. Hence, a further object of the invention provides for the use of a genetically modified plant or part thereof or of an extract as described in a food product or nutritional supplement.

It is to be noted that unlike conventional soy derived sources of dietary isoflavones, daidzein and the derivatives thereof as provided by plants according to the invention may be incorporated into food products without adversely affecting the flavour profile of such products. In this way an additional problem in the art is solved by the present invention.

A further object of the invention is therefore to provide a food product comprising a genetically modified plant or part thereof according to the description above. Preferably a food product according to the invention will be frozen to allow the content of daidzein and/or its derivatives to remain stable on storage.

In a most preferred embodiment a food product according to the invention is selected from the group comprising prepacked mixed salads, soups, spreads, sauces, fruit/cereal bars and ice creams.

A nutritional supplement comprising an extract of a plant or part thereof as described above is also provided by the present invention.

It is a further object of the invention to provide a process for increasing the content of daidzein and/or derivatives thereof in a plant or part thereof, wherein said process comprises the steps;

(i) selecting a non-isoflavone producing plant wherein said plant or part thereof is active in anthocyanin and flavonol biosynthesis;

(ii) genetically modifying said plant to increase the activity of chalcone reductase and isoflavone synthase in said plant or part thereof.

In a first embodiment, the process of the invention further comprises genetically modifying said plant or part thereof to increase the activity of a chalcone isomerase wherein said chalcone isomerase is capable of catalysing the conversion of 4,2',4'-trihydroxychalcone to 7,4'-dihydroxyflavanone. In this way the process achieves the synergistic increase in the content of daidzein and/or its derivatives.

A further embodiment wherein the activity of chalcone reductase and isoflavone synthase are to be increased comprises a process as disclosed above wherein one or more nucleotide sequences according to sequence identification numbers 1 and 3, or functional equivalents thereof are stably integrated into the genome of said plant.

To achieve the desired increase in activity of chalcone isomerase a preferred embodiment comprises a process as disclosed above additionally comprising stably integrating into the genome of said plant one or more nucleotide sequence according to sequence identification number 5, or functional equivalents thereof.

In a most preferred embodiment the process according to the invention relates to a plant or part thereof selected from the group comprising, but not resticted to, tobacco, *Lactuca* sp., broccoli, asparagus, red cabbage, potato, spinach, rhubarb, red onion, shallot, aubergine, radish, Swiss chard, purple basil, watermelon and berries such as strawberries.

DETAILED DESCRIPTION OF THE INVENTION

A sequence encoding a biosynthetic enzyme for increasing the tissue content of daidzein and/or daidzein derivatives may be a genomic or cDNA clone, or a sequence which in proper reading frame encodes an amino acid sequence which is functionally equivalent to the amino acid sequence of the biosynthetic gene encoded by the genomic or cDNA clone. A functional derivative can be characterised by an insertion, deletion or a substitution of one or more bases of the DNA sequence, prepared by known mutagenic techniques such as site-directed mutagenesis or derived from a different species.

For the performance of the present invention any nucleotide sequences encoding an enzyme with the biological function of a chalcone reductase, isoflavone synthase or chalcone isomerase may be used in the transformation of a suitably selected plant to increase these enzyme activities with said plant or part thereof.

Biological function of a nucleotide sequence encoding a chalcone reductase can be assessed by a standard assay (Welle et al., 1988 FEBS letter 236:221-225; Welle et al., 1991 Eur J Biochem 196:423-430; Welle and Schroder, 1992 Arch. Biochem. Biophys 293:377-381). To obtain protein, the nucleotide sequence is sub-cloned into a prokaryotic expression vector, such as pTZ19R (Pharmacia), and transformed into *Escherichia coli*. Selected *E. coli* clones harbouring the nucleotide sequences of interest are grown to a culture density of $A_{600}$=0.6-1 before inducing expression with 1 mM isopropyl β-D-thiogalctopyranoside (IPTG) for 2.5 hours. Following induction, bacteria are harvested by centrifugation and resuspended in 0.1M potassium phosphate, 0.6 mg/ml lysozyme and 1.2M EDTA and placed on ice for 45 min to lyse. The lysate is centrifuged at 16000 g for 20 min and an aliquot of supernatant used in the chalcone reductase assay.

Chalcone reductase activity is assayed in a final volume of 120 μl, comprising 80 μl chalcone reductase protein extract, 10 μmol potassium phosphate pH 5.0, 0.12 μmol NADPH, 1 nmol 4-coumaroyl CoA, 1.5 nmol [2-$^{14}$C] malonyl-CoA, 22.2 fkat pure soybean CHS (~3 μg). Reactions are run for 60 min at 30° C. before the reaction products are extracted in 200 μl ethyl acetate. The organic phase is separated by centrifugation, concentrated in vacuo and separated by thin layer chromatography using 15% acetic acid (presence of chalcone isomerase) or CHCl$_3$/acetic acid/water (10:9:1) (absence of chalcone isomerase). The identity of 6'-deoxychalcone is established by co-chromatography with a reference sample.

Suitable CHR encoding sequences already known in the art comprise; Alfalfa (*Medicago sativa*): accession numbers CHR1a-X82366, CHR1b-X82367, CHR2a-X82368, CHR7-U13925, CHR12-U13924; Chickpea (*Cicer arietinum*) accession number AB024989; Soybean (*Glycine max*) accession number X55730; Liquorice (*Glycyrrhiza glabra*) accession numbers CHRa-D86558, CHRb-D86559;

Alternatively suitable CHR encoding sequences may be isolated from other species. Sequence alignment of CHR's already known in the art, show two conserved regions Met-Pro-Val-Val-Gly-Met-Gly-Ser-Ala (Seq. ID No.7) and Ala-Ile-Ile-Glu-Ala-Ile-Lys-Gln (Seq. ID. No. 8) identified toward the 5' end of the coding sequence. Degenerate primers 327 and 328 (see FIG. 4) are designed to each of these coding sequences respectively. Sequences encoding CHR are isolated by polymerase chain reaction using primers 327 and 328 in conjunction with a dT$_{17}$ primer and using a 3' cDNA library target. The resulting fragments were cloned into a pT7 vector and sequenced. Alignment of these sequences with those known in the art would allow provisional identification. To obtain full-length coding sequence, 5' and 3' sequence can be obtained using standard 5'RACE and 3'RACE procedures as disclosed in example 1 (1.3.3).

A nucleotide sequence encoding an enzyme with isoflavone synthase activity may also be determined by a standard assay, wherein yeast microsomes are prepared from control WHT1 and strains expressing a cytochrome P450 cDNA according to the methods of Pompon et al., (Methods Enzymol. 272, 51-64). The assay is carried out according to Jung et al., (Nature Biotech 2000, vol 18 February 200, p208-212). The protein content of each microsome preparation is assayed using the Bradford protein micro assay (Bio-Rad. Hecules. CA). From 30 to 150 μg of microsomal proteins are incubated at room temperature in 80 mM K$_2$HPO$_4$, 0.5 mM glutathione. 20% (wt/vol) sucrose, pH 8.0 with 100 μM naringenin or 100 μM liquiritigenen substrate and 40 nmol of NADPH added per each 100 μl of final reaction volume. Following incubation, reactions are extracted with ethyl acetate. Samples assayed on a Hewlett-Packard 1100 series HPLC system using either a LiChrospher RP-C18 column (5 m 250×3 mm) or a Phenomenexz Luna C18 (2) column (3 u; 150×4.6 mm).

On the first column samples in ethyl acetate of candidate cDNA assays are isocratically separated for 5 min employing 65% methanol as a mobile phase. For the second column samples are evaporated and resuspended in 80% methanol and then separated using a 10 min linear gradient from 20% methanol/80% 10 mM ammonium acetate, pH 8.3 to 100% methanol at a flow rate of 1 ml min$^{-1}$ or using 65% methanol as mobile phase for isocratic elution. Genistein and daidzein are monitored by the absorbance of 260 nm. Using authentic naringinen, liquiritigen, genistein and daidzein (Indofine Chemical, Somerville NI) dissolved in ethanol as standards for calibration peak areas are converted to nanograms.

To confirm the identity of genistein and daidzein, samples are evaporated and resuspended in 25% acetonitrile in water and assayed on a Hewlett-Packard/Micromass LC/MS by running 25 μl on a Zorbax Eclipse XDB-C8 reverse-phase column (3×150 mm 3.5 μm) isocratically with 25% solvent B (0.1% formic acid in acetonitrile) in solvent A (0.1% formic acid in water). Mass spectrometry is done by electrospray scanning from 200 to 400 m/e, using −6 volt cone voltage. The diode array signals were monitored between 200 and 400 nm in both instruments.

Suitable IFS sequences already known in the art include Mung Bean accession number AF195807; Red Clover accession number AF195811; and Snow Pea accession number AF195812.

Alternatively suitable IFS cDNAs may be isolated from other species. Jung et al. (Nature Biotech 2000, vol 18 February 200, p208-212) describe how mung bean sprouts and snow pea sprouts were obtained from the grocery store. Seeds for alfalfa, red clover, white clover, hairy vetch and lentil can be obtained from Pinetree Garden Seeds (New Gloucester, Me.) seeds for lupine cv. Russel Mix were obtained from Botanical Interests (Boulder, Colo.), and seeds for sugarbeet were obtained from a commercial source.

Seedlings were grown and RNA prepared using TRIzol Reagent (Gibco BRL) and first-strand cDNA was prepared as described above. OligodT was used as the reverse transcription primer in all cases except with white clover for which random hexamers were used as the reverse transcription primer: Polymerase chain reaction amplifaction was carried out using Advantage-GC cDNA polymerase mix (Clontech) using primer set one 5'ATGTTGCTGGAACTTGCACTT-3' (Seq ID. No. 9) and 5'TTAGAAAGGAGTTTAGATG-CAACG-3' (Seq. ID. No. 10) or the nested primer set two: 5'TGTTTCTGCATTGCGTCCCAC-3' (Seq. ID. No. 11) and 5'-CCGATCCTTGCAAGTGGAACAC-3' (Seq. ID. No. 12) as follows: Mung bean and red clover PCR products amplified using primer set one were cloned directly into pCR2.1.

For white clover, lentil, hairy vetch, alfalfa, lupine, and beet a first PCR with primer set one was followed by a second primer set two, and the resulting fragments cloned. For snow pea, a first PCR with primer set one was followed by a second PCR with high annealing temperature (60° C.) using primer set one. The expected size product was gel purified and used as a template in a third PCR with the high annealing temperature and primer set one. The resulting product was cloned into pCR2.1. All PCR fragments in pCR2.1 were sequenced. All alignments were carried out using DNAStar MegAlign software version 4.05 and the Clustal algorithm set to default parameters.

The coding regions for accession numbers AF195807 (mung bean). AF195811 (red clover), and AF195812 (snow pea) were amplified and cloned into pRS315-gal using "gap repair" and microsomes were produced and assayed as described above.

A nucleotide sequence encoding an enzyme with chalcone isomerase activity capable of catalysing the conversion of 4,2',4'-trihydroxychalcone to 7,4'-dihydroxyflavanone may be determined by a standard assay (Dixon et al., 1982 Biochem. Biophys Acta 715: 25-33; Mol et al., 1985 Phytochemistry 24: 2267-2269, Terai et al., 1996 Protein Expression and Purification 8:183-190). To obtain protein, the nucleotide sequence is sub-cloned into a prokaryotic expression vector, such as pET vectors (Invitrogen), and transformed into *Escherichia coli*. Selected *E. coli* clones harbouring the nucleotide sequences of interest are grown to a culture density of $A_{600}$=0.6-1 before inducing expression with 1 mm isopropyl β-D-thiogalctopyranoside (IPTG) for 2.5 hours.

Following induction, bacteria are harvested by centrifugation and resuspended in 0.1M potassium phosphate, 0.6 mg/ml lysozyme and 1.2M EDTA and placed on ice for 45 min to lyse. The lysate is centrifuged at 16000 g for 20 min and an aliquot of supernatant used in the chalcone isomerase assay.

Chalcone isomerase activity is assayed in a final volume of 1 ml, comprising either 18.4 μm tetrahydroxychalcone (naringenin chalcone) or 12.7 μg trihydroxychalcone (isoliquiritigenin) substrate, chalcone isomerase protein extract, 5% (w/v) bovine serum albumin and 0.1M potassium phosphate buffer (pH5.8). Chalcone isomerase activity against both tri- and tetra-hydroxychalcone substrates is detected by a decrease in absorption at 385 nm.

Suitable CHI sequences already known in the art comprise those derived from; French bean (*Phaseolus vulgaris*) accession number X16470; Kudzu vine (*Pueraria montana* var. *lobata*): accession number D63577; Soybean (*Glycine max*): accession number AF276302; Alfalfa (*Medicago sativa*): accession number M910079; Garden Pea (*Pisum sativum*): accession number U03433.

Alternatively the well-established correlation between CHI function and structure enables suitable CHI sequences to be isolated from other sources. Numerous cloning strategies have been shown in the art to be effective at isolating CHI cDNAs and may be adopted by the person skilled in the art to identify alternative CHI encoding sequences.

Shirley, B. W., et al., (Plant Cell, Vol. 4, 333-347 1992) describes a PCR based approach to obtaining CHI cDNA from *Arabidopsis* wherein the identification of consensus sequences for primer design as well as PCR reaction conditions are disclosed. Sparvoli, F. et al., (Plant Mol. Biol. 24: 743-755, 1994) describes the cloning of CHI from a cDNA library by using heterologous Antirrhinum CHI cDNA probes. Grotewold E. et al., (Mol. Gen. Genet. (1994) 242: 1-8) describes the isolation and characterisation of a maize gene encoding CHI, the cloning strategy and suitable primers.

The literature outlined above clearly demonstrates that corresponding CHI sequences from other plants; alternative cloning strategies for other CHI genes; knowledge of consensus sequences for the generation of primers; appropriate PCR conditions are known in the art. The person skilled in the art is therefore able to identify and use alternative CHI sequences for the transformation according to the present invention.

Gene constructs according to the invention either comprise one or more nucleotide sequences encoding chalcone reductase and isoflavone synthase, or comprise one or more nucleotide sequences encoding chalcone reductase, isoflavone synthase and chalcone isomerase depending on the magnitude of increase sought.

The gene sequences of interest will be operably linked (that is, positioned to ensure the functioning of) to one or more suitable promoters which allow the DNA to be transcribed. Suitable promoters, which may be homologous or heterologous to the gene (that is, not naturally operably linked to a gene encoding an enzyme for flavonoid biosynthesis), useful for expression in plants are well known in art, as described, for example, in Weising et al., (1988) Ann. Rev. Genetics 22:421-477. Promoters for use according to the invention may be inducible, constitutive, or tissue-specific or have various combinations of such characteristics.

Useful promoters include, but are not limited to constitutive promoters such as carnation etched ring virus (CERV) promoter, cauliflower mosaic virus (CaMV) 35S promoter, or more particularly the enhanced cauliflower mosaic virus promoter, comprising two CaMV 35S promoters in tandem (referred to as a "Double 35S" promoter). These would have the effect of increasing isoflavonoid levels throughout a plant.

Accordingly, the invention provides in a further aspect a gene construct in the form of an expression cassette comprising as operably linked components in the 5'-3' direction of transcription, one or more units each comprising a suitable promoter in a plant cell, a plurality of nucleotide sequences selected from the group comprising sequences encoding a CHR and IFS and a suitable transcriptional and translational termination regulatory region. More preferably said group comprises sequences encoding CHR, IFS and a CHI capable of catalysing the conversion of 4,2',4'-trihydroxychalcone to 7,4'-dihydroxyflavanone.

The promoter and termination regulatory regions will be functional in the host plant cell and may be heterologous or homologous to the plant cell and the gene. Suitable promoters which may be used are described above.

The termination regulatory region may be derived from the 3' region of the gene from which the promoter was obtained or from another gene. Suitable termination regions, which may be used, are well known in the art and include *Agrobacterium tumefaciens* nopaline synthase terminator (Tnos), *Agrobacterium tumefaciens* mannopine synthase terminator (Tmas), the rubisco small subunit terminator (TrbcS) and the CaMNV 35S terminator (T35S). Particularly preferred termination regions for use according to the invention include the Tnos and TrbcS termination regions.

Such gene constructs may suitably be screened for activity by transformation into a host plant via *Agrobacterium tumefaciens* co-transformation and screening for daidzein levels.

Conveniently, the expression cassette according to the invention may be prepared by cloning the individual promoter/gene/terminator units into a suitable cloning vector. Suitable cloning vectors are well known in the art, including such vectors as pUC (Norrander et al., (1983) Gene 26:101-106), pEMBL (Dente et al., (1983) Nucleic Acids Research 11:1645-1699), pBLUESCRIPT (available from Stratagene), pGEM (available from Promega) and pBR322 (Bolivar et al., (1977) Gene 2:95-113). Particularly useful cloning vectors are those based on the pUC series. The cloning vector allows the DNA to be amplified or manipulated, for example by joining sequences. The cloning sites are preferably in the form of a polylinker, that is a sequence containing multiple adjacent restriction sites, to allow flexibility in cloning.

Preferably the DNA construct according to the invention is comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al., Cloning Vectors. A laboratory manual, Elsevier, Amsterdam (1986). Particularly suitable vectors include the Ti plasmid vectors.

Transformation techniques for introducing the DNA constructs according to the invention into host cells are well known in the art and include such methods as micro-injection, using polyethylene glycol, electroporation, or high velocity ballistic penetration. A preferred method for use according to the present invention relies on *Agrobacterium tumefaciens* mediated co-transformation.

After transformation of the plant cells or plant, those plant cells or plants into which the desired DNA has been incorporated may be selected by such methods as antibiotic resistance, herbicide resistance, tolerance to amino-acid analogues or using phenotypic markers.

Various assays within the knowledge of the person skilled in the art may be used to determine whether the plant cell shows an increase in gene expression, for example, Northern blotting or quantitative reverse transcriptase PCR (RT-PCR). Whole transgenic plants may be regenerated from the transformed cell by conventional methods. Such transgenic plants having improved daidzein levels may be propagated and crossed to produce homozygous lines. Such plants produce seeds containing the genes for the introduced trait and can be grown to produce plants that will produce the selected phenotype.

Plants or parts thereof which have been modified in accordance with the present invention may be the used as a source of daidzein and/or one or more of its derivatives in the form of an enriched extract or a substantially pure form.

Food products which comprise the plants, plant parts or extracts thereof in accordance with the present invention enable the consumer to take full advantage of the health benefits associated with increased isoflavone uptake while at the same time avoiding the adverse flavour associated with soy derived isoflavones in the prior art.

Salad leaves are particularly suited to genetic transformation by the process of the invention and therefore species of lettuce (*Lactuca* sp.) such as *Lactuca sativa* e.g. 'Red Oak Leaf', 'Red Leprechaun'; *Lactuca sativa* group Butterhead lettuce e.g. Mira, Redcross; *Lactuca sativa* group Cos lettuce e.g. 'Romaine Red Cos', Four Seasons Red', Seville; *Lactuca sativa* group Crisp lettuce e.g. 'Red Salad Bowl', Red Grenoble'; *Lactuca sativa* group Cutting lettuce e.g. 'Lollo Rosso', Revolution transformed in accordance with the present invention provide a ideal means of supplementing dietary needs and may be provided washed and pre-packed to the consumer.

Fruit containing snack bars or breakfast cereals provide a convenient means of supplementing the human diet with isoflavones. Fruit pieces derived from a plant according to the invention are suitably dried to from 10 to 90%, preferably 20 to 60%, most preferably about 40% of their fresh weight to give shelf stability and incorporated into a bar or cereal product.

Fruits with high levels of daidzein and/or daidzein derivatives in accordance with the invention are also be ideally incorporated into yoghurts and ice creams or to flavour fruit drinks.

Suitable fruits for these food products would include raspberries, strawberries, blackcurrants, red currants, blueberries and blackberries.

Plants or parts thereof which have been genetically modified in accordance with the present invention may also provide a source of an extract rich in daidzein and/or its derivatives or a purified form thereof for inclusion in products such as nutritional supplements, calorie controlled drinks and low fat spreads.

A large body of evidence supports the cosmetic and medical health benefits that can be attributed to human dietary consumption of isoflavones and in particular daidzein. These include: activity as both estrogenic and anti-estrogenic agents (Coward et al., 1993; Martin, et al., 1996); anticancer effects associated with phytoestrogenic activity (Lee et al., 1991; Adlercreutz et al., 1991); anticancer effects associated with inhibition of several enzymes including DNA topoisomerase and tyrosine protein kinase (Akiyama, et al., 1987; Uckun, et al., 1995); suppression of alcohol consumption (Keung and Vallee, 1993; Keung et al., 1995); antioxidant activity (Arora et al., 1998; Tikkanen et al., 1998); increasing bone remineralisation (Tomonaga et al., 1992; Draper et al., 1997); and beneficial cardiovascular effects (Wagner et al., 1997).

The present invention may be more fully understood by reference to the accompanying figures in which:

FIG. 1: shows the pea chalcone reductase DNA sequence (SEQ ID No. 1) and its corresponding protein sequence (SEQ ID No. 2).

FIG. 2: shows the soy isoflavone synthase DNA sequence (SEQ ID No.3) and its corresponding protein sequence (SEQ ID No. 4)

FIG. 3: *Lotus corniculatus* chalcone isomerase DNA sequence (SEQ ID No. 5) and its corresponding protein sequence (SEQ ID No. 6)

FIG. 4: provides primer sequences used in accordance with the invention.

FIG. 5: illustrates Plasmid maps of pPV5LN, pPE2, pPE5, pPE9, pPE11, pPE15, pPE51, pPE120 and pPE125.

Figure 6A:
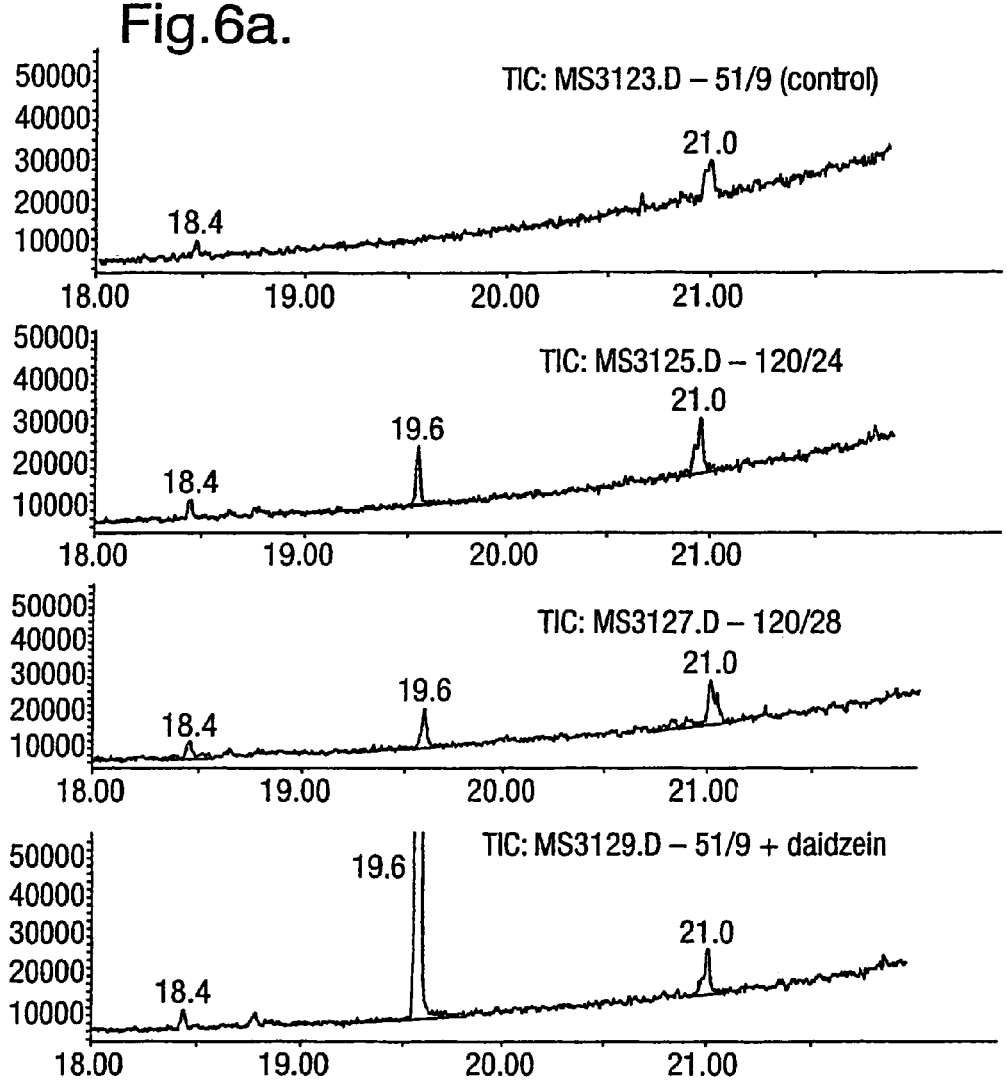
Figure 6B:
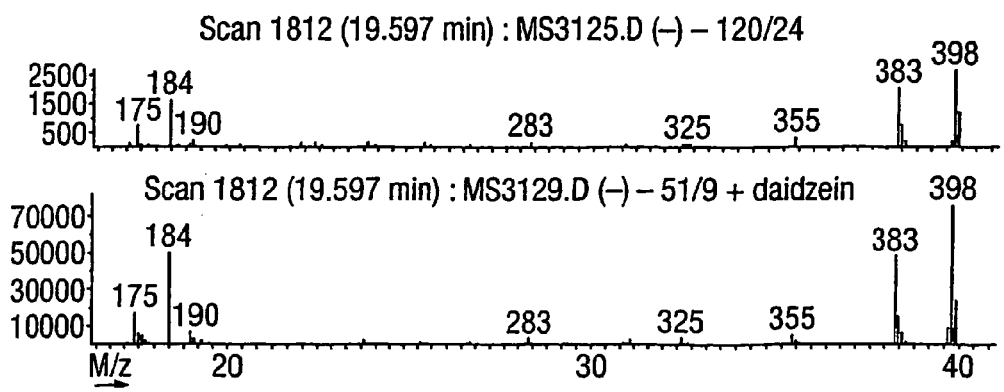

FIG. 6: illustrates GC-MS analysis of tobacco petal extracts from representative tobacco transfomants, pPE120/24, pPE120/26 and pPE51 spiked with an authentic daidzein standard. A. Peak with retention time corresponding with authentic daidzein (RT=19.60) is present I pPE120/24 and pPE120/26 transformants. B. Selected ion monitoring of pPE120/24 and pPE51/9 spiked with an authenitc daidzein standard shows characteristic peaks in pPE120/24.

Figure 7:
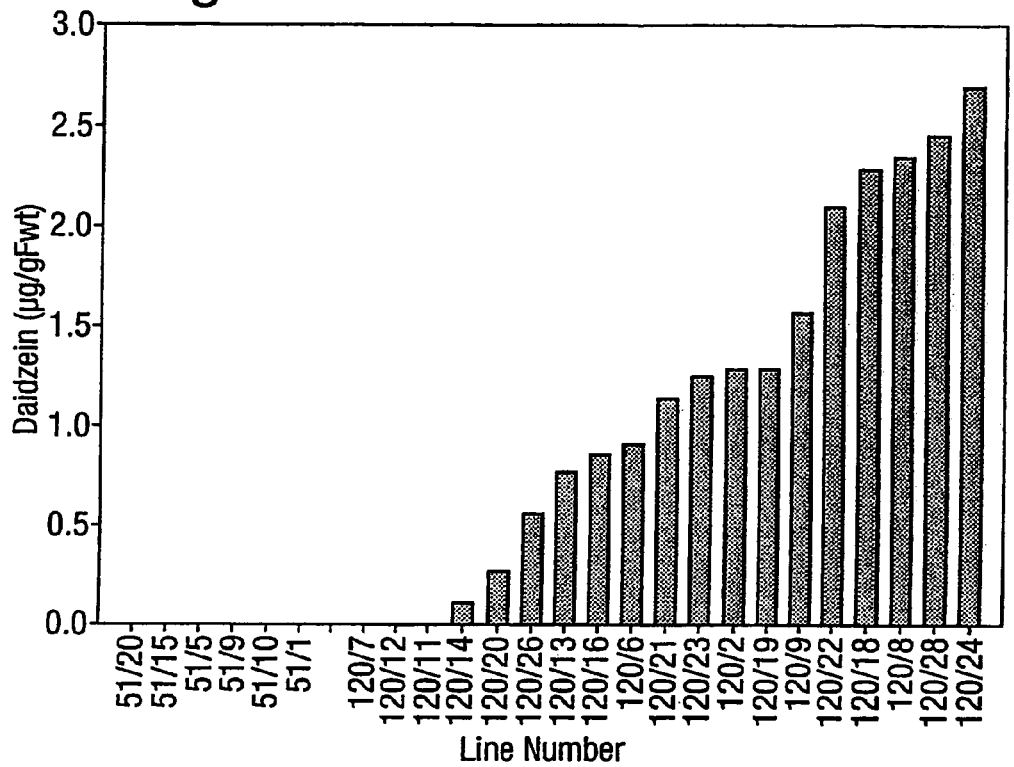

FIG. 7: illustrates accumulation of daidzein in petal tissue from tobacco transformants harbouring constructs encoding chalcone reductase and isoflavone synthase (pPE120) activitites with controls (pPE51). Ethanol extracts from petals were hydrolysed and analysed by HPLC.

Figure 8:
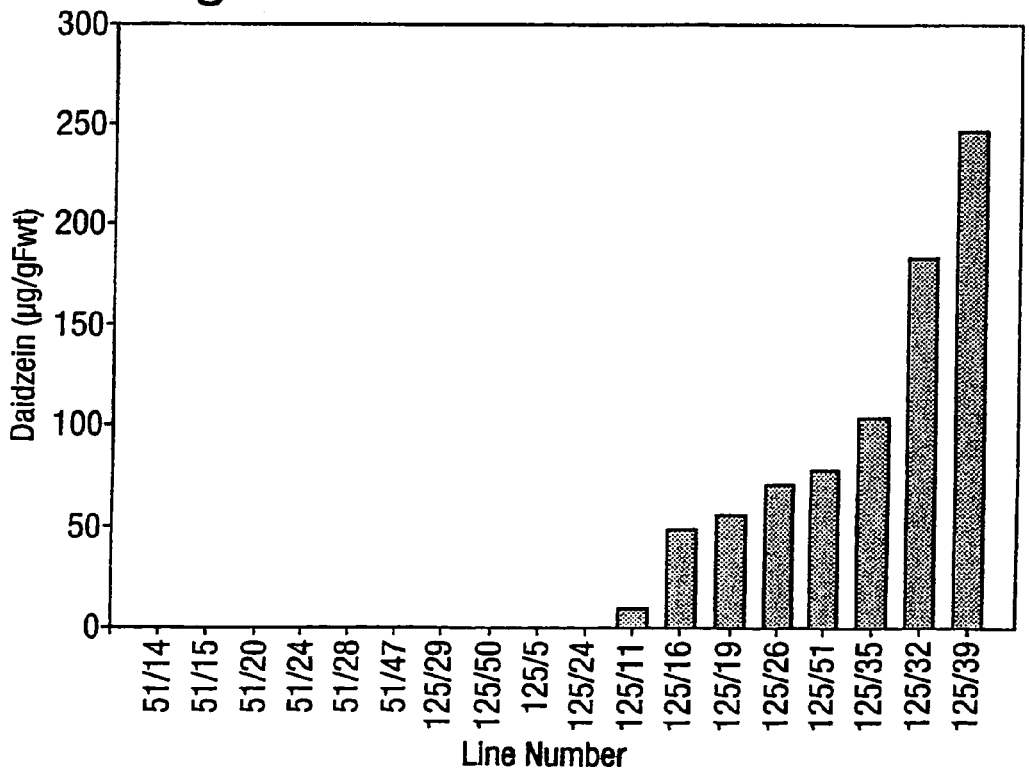

FIG. 8: illustrates accumulation of daidzein in petal tissue from tobacco transformants harbouring constructs encoding chalcone reductase, chalcone isomerase and isoflavone synthase (pPE125) activitites with controls (pPE51). Ethanol extracts from petals were hydrolysed and analysed by HPLC.

EXAMPLE 1 cDNA Cloning of Chalcone Reductase, Chalcone Isomerase and Isflavone Synthase and the Generation and Analysis of Transgenic *N. tabacum*

1.1 Plant Material

All experiments can be performed using normally available tobacco (*Nicotiana tabacum*) genotypes as the starting material. *N. tabacum* cultivar SR1 is such a genotype. Plants of *N. tabacum* cultivar SR1 were grown in controlled temperature growth rooms with a 16-hour photoperiod at a temperature of 25° C.

1.2 Bacterial Strains

*Escherichia coli* strain XL1-Blue: recA1, endA1, gyrA96, thi-1, hsdR17, supE44, relA1 lac [F'proAB laCl$^q$ZΔM15 Tn10 (Tet$^r$)] (Stratagene Europe, The Netherlands). Transformation of *E. coli* XL1-Blue was performed using the method of Hanahan (1983). *Agrobacterium tumefaciens* LBA4404 (Hoekema, 1985). Transformation of *Agrobacterium tumefaciens* LBA4404 was performed according to Shen and Forde (1989).

1.3 Gene Cloning

1.3.1 Total RNA Isolation

RNA was isolated from *Lotus corniculatus* (*Lotus*), *Glycine max* (soybean), *Pisum sativum* (pea) and *Medicago sativa* (alfalfa) leaf tissue using a Purescript RNA isolation kit (Pharmacia) according to manufacturer's instructions.

1.3.2 cDNA Synthesis

5' cDNA library construction: 2 µg of RNA isolated from either *Lotus*, soybean, pea or alfalfa tissue was heated to 65° C. for 10 minutes, then snap cooled on ice. The RNA was reverse transcribed in a 20 µl reaction for 90 minutes at 42° C. using 10 units of stratascript (Gibco-BRL) in 1×rt buffer (Gibco BRL), 30 mM dNTPs (DATP, dCTP, dTTP, dGTP) (Pharmacia), 0.1M DTT, 1 U/µl RNasin (Roche) and 50 pmoles random hexamers. The random primed cDNA was then purified using a Gibco-BRL pcr purification kit (according to manufacturer's instructions). The purified cDNA was then poly A tailed in 50 µl of 1× tailing buffer (Roche), 1 mM DATP (Roche), 1 unit terminal transferase (Roche) at 37° C. for 5 minutes then denatured at 80° C. for 15 minutes.

3' cDNA library construction: 2 µg of RNA isolated from either *Lotus*, soybean, pea or alfalfa tissue was heated to 65° C. for 10 minutes, then snap cooled on ice. The RNA was reverse transcribed in a 20 µl reaction for 90 minutes at 42° C. using 10 units of stratascript in 1×RT buffer 30 mM dNTPs, 0.1M DTT, 1 U/µl Rnasin and 5 pmoles oligo $dt_{17}$.

1.3.3 PCR Amplification

Library PCR amplification: Song of 3' cDNA was PCR amplified in 50 µl of 1×PCR buffer (Roche), 20 mM dNTPs 25 pmoles 5' primer, 25 pmoles 3' primer, 2.5 units Taq DNA polymerase (Roche), 0.25 units pfu turbo DNA polymerase (Stratagene). Cycling conditions were; 30 cycles of 94° C. for 30 seconds, 55° C. for 30 seconds, 72° C. for 2 minutes, using a Perkin Elmer PCR machine. The initial denaturing step (94° C.) was extended to 2 minutes.

Vector PCR amplification: 1 ng of a vector was PCR amplified in 50 µl of 1×PCR buffer (Stratagene), 20 mM dNTPs 25 pmoles 5' primer, 25 pmoles 3' primer, 5 units pfu turbo DNA polymerase. Cycling conditions were; 30 cycles of 94° C. for 30 seconds, 55° C. for 30 seconds, 72° C. for 2 minutes. The initial denaturing step (94° C.) was extended to 2 minutes.

5' Rapid Amplification of cDNA Ends (5'race): 50 ng of 5' cDNA was complemented in 50 µl of 1×PCR buffer, 20 mM dNTPs, 5 pmoles oligo $dt_{17}$, 1.25 units Taq DNA polymerase, 0.125 units pfu turbo DNA polymerase. Conditions were 94° C. for 2 minutes, 42° C. for 2 minutes, 72° C. 45 minutes. The cDNA was amplified by adding the following; 25 pmoles 5' $R_O$ primer, 25 pmoles primer $R_O$, 1.25 units Taq DNA polymerase, 0.125 units pfu turbo DNA polymerase to the reverse transcription reaction. Cycling conditions were; 30 cycles of 94° C. for 30 seconds, 55° C. for 30 seconds, 72° C. 2 minutes. The initial denaturing step was extended to 2 minutes. 1 µl of this PCR reaction was re-amplified in 50 µl of 1×PCR buffer, 20 mM dNTPs 25 pmoles 5'$R_O$ primer, 25 pmoles $R_O$ primer, 2.5 units Taq DNA polymerase, 0.25 units pfu turbo DNA polymerase. Cycling conditions were; 30 cycles of 94° C. for 30 seconds, 55° C. for 30 seconds, 72° C. 30 seconds. The initial denaturing step was extended to 2 minutes.

3' Rapid Amplification of cDNA Ends (3'race): 50 ng of 3' cDNA was amplified in 50 µl of 1×PCR buffer, 20 mM dNTPs, 25 pmoles 5'$R_O$ primer, 25 pmoles primer $R_O$, 2.5 units Taq DNA polymerase, 0.25 units pfu turbo DNA polymerase. Cycling conditions were; 30 cycles of 94° C. for 30 seconds, 55° C. for 30 seconds, 72° C. 2 minutes. The initial denaturing step was extended to 2 minutes. 1 µl of this PCR reaction was re-amplified with 5'$R_I$ primer and $R_I$ as before with cycling conditions: 30 cycles of 94° C. for 30 seconds, 55° C. for 30 seconds, 72° C. I minute. The initial denaturing step was extended to 2 minutes.

1.3.4 Isolation and Cloning of Amplified Products

Fragments generated by PCR were analysed on an ETBr-1.2% agarose TBE (45 mM Tris-borate, 1 mM EDTA) gel. DNA fragments were isolated from the gel using a Gibco-BRL gel extraction kit according to manufacturer's instructions and cloned into a pT7 TA cloning vector (Novagen).

1.3.5 Digesting DNA with Restriction Enzymes

PCR amplifications or 2 µg of plasmid DNA were digested with 10 units of each appropriate restriction enzyme (Roche) in the recommended buffer at 37° C. for 2 hours. Digests were separated on EtBr-1.2% agarose TBE gel: The desired fragments were excised and purified using the Gibco-BRL gel extraction kit according to manufacturer's instructions.

1.3.6 Construction of Synthetic Linkers

1 µg of sense and anti-sense oligonucleotides were annealed together by heating to 94° C. for 5 minutes in 1× ligation buffer and then cooled to room temperature over a period of 30 minutes.

1.3.7 De-Phosphorylation of DNA Fragments

Vector DNA fragments were incubated in 50 µl of 1×sip (Roche) buffer with 0.5 units shrimp intestinal phosphorylase (Roche) at 37° C. for 15 minutes and then denatured at 80° C. for 5 minutes.

1.3.8 Sub-Cloning into Vectors

DNA fragments of interest were ligated into appropriate vectors in a ratio of 5:1 in a final volume of 20 µl containing 1× ligation buffer (Roche), 2 units of T4 DNA ligase (Roche) at 4-8° C. for 16 hours.

1.3.9 Preparation and Transformation of Competent *E. coli*

To prepare competent cells a culture of XL1-Blue (from a single colony) was grown up overnight at 37° C., 225 r.p.m. in 10 ml Lennox broth containing 12.5 µg/ml tetracycline. 1 ml from this overnight culture was transferred into 100 mls of fresh, pre-warmed, Lennox broth and cultured for a further 2 hours until the $OD_{600}$ was in the range 0.3 to 0.6. The cells were then recovered by centrifugation at 4500 g for 10 minutes at 4° C. The cells were washed in 50 ml 100 mM $CaCl_2$, before resuspending in a final volume of 5 ml 100 mM $CaCl_2$. The cells were then placed on ice for 1 hour.

Transformations were performed as follows: One-fifth (4 µl) of the ligation reaction was added to 200 µl competent cells. The mixture was incubated on ice for 30 minutes then heat shocked at 42° C. for 40 seconds. 300 µl of 2YT was then added to the mixture before incubating at 37° C., 225 r.p.m. for 30 minutes. The transformations were then plated out on Lennox agar containing 100 µg/ml carbenicillin or 50 µg/ml kanamyicin and incubated at 37° C. overnight.

1.3.10 Identification and Screening of *E. coli* Recombinants

Positive transformants were identified by amplifying DNA from a single colony in a 50 µl reaction containing the following mixture, 1×pcr buffer, 0.2 mM dNTPs, 25 pmoles 5' primer, 25 pmoles 3' primer, 1.25 units Taq DNA polymerase. Cycling conditions were 94° C. for 30 seconds, 55° C. for 30 seconds, 72° C. 1 minute, for 30 cycles. The initial denaturing step was extended to 2 minutes. The pcr amplifications were then analysed on EtBr-1.2% agarose TBE gels.

1.3.11 Extraction and Purification of Plasmid DNA

Selected colonies were grown up overnight in 50 mls of 2TY broth containing either 100 µg/ml carbenicillin or 50 µg/ml kanamycin (as appropriate) at 225 r.p.m. at 37° C. The cells were recovered by centrifugation at 4500 g for 10 minutes at 4° C. The bacterial pellet was resuspended in 4 ml of solution 1 (25 mM Tris.Cl pH8.0, 10 mM EDTA), then 8 ml of solution 2 (0.2N NaOH, 1% SDS) was added, and left at room temperature for 5 minutes to lyse the cells. 6 ml of ice-cold solution 3 (3M potassium, 5M acetate) was added and the mixture incubated on ice for 15 minutes. The bacterial lysate was then centrifuged at 15000 g, 4° C. for 20 minutes, and the supernatant was filtered through 4 layers of miracloth (CalBiochem). 10 mls of Isopropanol was added to precipitate the DNA and the precipitate spun for 15 minutes at 15000 g, at room temperature. The pellet was resuspended in 1 ml of TE (10 mM Tris.Cl pH7.6, 1 mM EDTA) with 10 µg/ml RNase A and incubated at 50° C. for 30 minutes to remove contaminating RNA. The solution was extracted twice with an equal volume of phenol/chloroform (1:1) then once with an equal volume of chloroform. The DNA was re-precipitated with 0.1 volume 3M NaAc pH5.2 and 0.7 volume isopropanol, then spun for 5 minutes at 10000 g, at room temperature. The pellet was washed in 70% ETOH then air dried and resuspended in TE at a final concentration of 1 µg/µl.

1.4 Vector Construction

Expression vectors were generated containing chalcone reductase (CHR), chalcone isomerase (CHI) and isoflavone synthase (IFS) cDNA's from *Pisum sativum*, *Lotus corniculatus* and *Glycine max* respectively. CHR, CHI and IFS transgenes were placed under the control of the double 35s promoter to give high levels of expression in tobacco tissues.

1.4.1 Construction of Plasmid pPV5LN

To construct pPV5LN, pUC19 was modified as follows. Firstly, plasmid pPV3 was constructed by removing the HindIII/EcoRI multiple cloning site from pUC19 and replacing it with a synthetic DNA fragment, destroying the original EcoRI and HindIII sites and introducing SgfI, HindIII, KpnI, EcoRI and XbaI restriction sites. This synthetic fragment was constructed by annealing the oligonucleotides 624 and 625 (FIG. 4). This resulted in plasmid pPV3.

The KpnI/EcoRI insert from pSJ30 containing the 2×35S-promoter sequence upstream of an ~1.9 kb coding sequence, followed by the Nos terminator sequence was ligated with pPV3 restricted with KpnI/EcoRI. This resulted in plasmid pPV5.

The ~1.9 kb coding sequence was then removed from pPV5 as a SalI/SacI fragment and replaced by a synthetic DNA fragment introducing NcoI, NheI and MunI restriction sites, while leaving the original SalI/SacI sites intact. This synthetic fragment was constructed by annealing the oligonucleotides 626 and 627 (FIG. 4). This resulted in plasmid pPV5L.

The sequence immediately 5' of the start codon ATG in pPV5L (CCACC) was replaced by the plant Kozak sequence TAAACC using PCR. Oligonucleotides 640 and 641 (FIG. 4) were used to amplify the 189 bp 3' fragment of the 2×35S promoter from vector pCP031 (van Engelen et al., 1994), modifying the Kozak sequence via oligonucleotide 641. pCP031 and the amplified fragment were then restricted with HindIII/EcoRV and EcoRV/NcoI respectively before ligation with pPV5L restricted with HindIII-NcoI to replace the promoter. This resulted in plasmid pPV5LN (FIG. 5).

1.4.2 Construction of Plasmid pPE-2

To construct the plasmid pPE-2, the multiple cloning site of pPV5LN was modified by the insertion of three oligonucleotide adapters. First, oligonucleotides 331 and 332 (FIG. 4) were annealed together and ligated with plasmid pPV5LN restricted with EcoRI-XbaI. This resulted in plasmid p5LNa. Next, the multiple cloning site from pPV5LN was amplified using oligonucleotides 248 and 191 (FIG. 4) and the amplification product restricted with XbaI and EcoRI. This product was then ligated, in conjunction with the annealed product of oligonucleotides 333 and 334 (FIG. 4) with p5LNa restricted with NcoI-EcoRI. This resulted in plasmid p5LNb. To construct plasmid pPE-2, oligonucleotides 329 and 330 were annealed together and ligated with plasmid p5LNb restricted with SfiI-HindIII. This resulted in plasmid pPE-2 (FIG. 5).

1.4.3 Construction of Plasmid pPE-5

To construct the plasmid pPE-5, the multiple cloning site of pSJ34 was modified by the insertion of an oligonucleotide adapter. First, oligonucleotides 337 and 338 (FIG. 4) were annealed together and ligated with plasmid pSJ34 restricted with HindIII-EcoRI. This resulted in plasmid pPE-5 (FIG. 5).

pSJ34 is a derivative of the binary vector pGPTV-Kan (Becker et al., 1992 Plant Mol. Biol. 20: 1195-1197) in which the BamHI site between the nptII selectable marker and the gene7 poly (A) signal was destroyed by 'filling-in' with klenow polymerase.

1.4.4 Construction of Plasmid pPE-9 (2×35S+kozak-*Lotus* CHI-Tnos)

*Lotus* CHI cDNA was amplified from the lotus 3' and the 5' cDNA library using primers 160/323 and 160/321 respectively (FIG. 4); the amplification products were then re-amplified using primers 198/324 and 198/322 respectively (FIG. 4). The amplified fragments were separated by electrophoresis and products 5a.3.19 and 2.11 respectively were cloned into the vector pT7 and sequenced with primers 152 and 191 (FIG. 4).

To verify the DNA sequence of the amplified fragments primers 386 and 387 were used to amplify the complete coding region of the CHI gene (in triplicate) from a lotus 3' cDNA library. The resultant fragments LCHI-A, LCHI-B and LCHI-C were cloned into vector pT7 and sequenced with primers 152 and 191. Clone LCHI-A was re-amplified with primers 386/403 and 402/387, the resultant fragments were digested with NcoI-PstI and PstI-NheI respectively and ligated into NcoI-XbaI opened PE-2 to create the vector PE-9 (2×35S+Kozak-*Lotus* CHI-tNOS in PE-2) (FIG. 5).

1.4.5 Construction of Plasmid pPE-11 (2×35S+kozak-Pea CHR-Tnos)

The chalcone reductase cDNA was amplified from a *Pisum sativum* leaf tissue 3' cDNA library using primers 384 and 385. The resulting 0.98 kb product was ligated with the PCR cloning vector pT7Blue [Novagen] and the sequence verified before further sub-cloning.

The chalcone reductase sequence was then amplified from the pT7Blue vector using oligonucleotides 384/362, 363/398, 399/400 and 401/385 (Table 1). The resulting amplification products were restricted with NcoI-NarI, NarI-BamHI, BamHI-MunI, and MunI-NheI respectively before ligation with pPE-2 restricted with NcoI-XbaI. This resulted in plasmid pPE-11 (FIG. 5).

1.4.6 Construction of Plasmid pPE-15 (2×35S+kozak-Soy IFS-Tnos)

The isoflavone synthase cDNA was amplified from a *Glycine max* leaf tissue cDNA library using primers 339/340, 341/342, and 343/344 (Table 1). The resulting amplification products were restricted with NcoI-ApaI, ApaI-SalI, and SalI-NheI respectively before ligation with pPE-2 restricted with NcoI-XbaI. This resulted in plasmid pPE-15 (FIG. 5).

1.4.7 Construction of Plant Transformation Vector pPE-120 (CHR-IFS)

The single gene constructs described above were used to construct the plasmid pPE120 as follows. Plasmids pPE-11 and pPE-15 were restricted with SalI-EcoRI and HindIII-SalI respectively. The 2×35S+kozak-Pea CHR-Tnos and 2×35S+kozak-Soy IFS-Tnos fragments were then ligated with pPE-5 restricted with HindIII-EcoRI. This resulted in plasmid pPE120 (FIG. 5).

1.4.8 Construction of Plant Transformation Vector pPE-125 (CHR-CHI-IFS)

To construct the plant transformation vector pPE125, plasmids pPE-9 and pPE-120 were restricted with SalI. The resulting 2×35S+kozak-*Lotus* CHI-Tnos fragment (from pPE-9) was then ligated with SalI linearised pPE-120. This resulted in plasmid pPE-125 (FIG. 5).

1.4.10 GPTV Control Plasmid

A GPTV-based binary plasmid, pPE51 (FIG. 5), containing the double CaMV 35s promoter and the nos poly(A) signal (Pd35s-Tnos) was used as control plasmid. This allows direct comparison between transformed control plants and plants containing the CHR, CHI and IFS constructs generated via a tissue culture procedure.

pPE51 was constructed by restricting pPE2 with EcoRI-HindIII. The 2×35S+kozak-Tnos fragment was then ligated with pPE5 restricted with HindIII-EcoRI. This resulted in plasmid pPE51 (FIG. 5).

1.5 *A. tumefaciens* Transformation

Binary plasmids of pPE120, pPE125, pPE130 and pPE51 were introduced into *Agrobacterium tumefaciens* strain LBA4404 by high voltage electroporation as described by Shen and Forde (1989). Briefly, electrocompetent cells of *A. tumefaciens* were prepared by inoculation of 50 ml of 2×YT medium (Sambrook et al., 1989) and culturing with shaking at 100 rpm at 28° C. until the culture reached an $OD_{600}$ of 0.5-0.7. The cells were cooled on ice, harvested by centrifugation and the supernatant discarded. The cells were then washed successively in 50, 25, 1 and 1 ml of cold 10% (v/v) glycerol before re-suspension in 0.5 ml 10% glycerol.

For transformation, 40 µl of cells were transferred to a pre-cooled 0.2 cm electroporation cuvette (Bio-Rad Laboratories). One µl of either pPE120 or pCJ102 plasmid DNA was mixed with the cell suspension on ice and an electric pulse applied immediately using a Gene Pulser with Pulse controller unit (Bio-Rad). For transformation, the field strength was 12.5 kV/cm, a capacitance of 25 µF and resistors of 400-600 ohms in parallel, giving time constants of 8-12 msec. The cells were immediately transferred to 1 ml 2×TY and shaken at 29° C. for 2 hours. Aliquots were then plated onto LB agar supplemented with kanamycin and incubated for 2-3 days at 29° C.

The presence and integrity of the plasmids in kanamycin resistant clones was established by PCR analysis using pPE120 (GPTV2 and 30035s; 340-GPTV1), pPE51 (30035S and GPTV2), pPE125 (GPTV2 and 30035s; 340-GPTV1; 248-403; 402-398), pPE130 (GPTV2-30035S) specific primers respectively (FIG. 4).

1.6 Stable Transformation of *Nicotiana tabacum* cv SR1

*A. tunefaciens* cells from PCR positive colonies were used to inoculate a 10 ml Lennox media broth containing kanamycin 50 :g/ml and rifampicin 50 :g/ml and incubated overnight with shaking (120 rpm) at 29° C. The overnight culture was centrifuged at 3000 g and the cell pellet resuspended in an equal volume of MS media (3% sucrose). Leaf segments were cut from young *Nicotiana tabacum* L. cv. SR1 leaves from plants grown in tissue culture. The leaf segments were placed directly into the *A. tumefaciens* suspension and co-incubated for 10 minutes.

The leaf segments were then transferred, axial surface down, to feeder plates (10 per plate) and placed at 22° C. for 2 days in low light. The leaf segments were then transferred, axial surface up, to tobacco shooting media supplemented with hormones, cefotaxime 500 :g/ml and kanamycin 50 :g/ml and placed in a growth room at 24° C. with a 16 hr photoperiod. After three weeks, callusing segments were transferred to fresh tobacco shooting media in vitro-vent [Melford Laboratories Ltd.] tissue culture vessels. Shoots were then excised from callused leaf segments and placed on tobacco shooting media without hormones containing cefotaxime 500 :g/ml and kanamycin 50 :g/ml.

Genomic DNA was isolated from shoots that had rooted and transgenic plants harbouring the constructs were selected following specific amplification of the CHR, CHI, IFS transgenes respectively.

Transgene positive plants were then potted up into a 50% perlite 50% compost mixture and placed in a propagator in a growthroom at 25° C. with a 16 h photoperiod (3000 lux). After 1 week the plants were removed from the propagator and subsequently potted up into 5-inch pots.

Petal tissue was harvested from each independent transformant and stored for subsequent analysis. When flowering had finished, each plant was cut-back and allowed to re-grow to form new flowers, from which seeds were harvested for propagation and analysis.

1.7 Extraction of Flavonoids and Isoflavonoids from Tobacco Tissues

Flavonoids and isoflavonoids were determined as their glycosides or as aglycones by preparing non-hydrolysed and hydrolysed extracts, respectively.

For extraction, tobacco petal tissues were harvested from fully open, mature flowers. To ensure representative analyses, all of the flowers (>10 per plant) were harvested at a similar developmental stage from each pPE120, pPE125 and corresponding pPE51 (control) plants. The flower was fractionated to remove stamen, carpel and corolla tube tissue and the remaining petal tissue was then flash frozen in liquid nitrogen before being stored at −80° C. The petal tissues (>10) from each plant were then ground to a fine powder to ensure a homogeneous mix. An aliquot from this mixture was then extracted for 30 min at room temperature (~22° C.) in 80% (v/v) ethanol at 100 mg/700 µl. Following extraction, the cell debris was removed by filtration through a 0.45 µm Millex-HV filter unit (Millipore Corp, USA). The filtrate was stored at −20° C. prior to HPLC analyses.

For hydrolysed extracts, 40 µl of 12M HCl was added to 360 µl from each petal extract, before incubating at 90° C. for 40 min.

Daidzin/genistin standards were hydrolysed under the same conditions as the petal extracts providing a control for the hydrolysis process.

1.8 Flavonoid and Isoflavonoid Analyses 1.8.1 HPLC Conditions for Flavonoid and Isoflavonoid Analysis After hydrolysis, an aliquot from each extract was filtered through a 0.2 µm PTFE disposable filter (Whatman). The filtrate (20 µl) from was injected into the HPLC system (HP1100, Agilent) via an autosampler maintained at 4° C.

The analytical column (Prodigy Phenyl-3, 4.6×150 mm, particle size 5 μm, (Phenomenex) was held at 30° C. Detection was by diode array, monitoring at 262, 280, and 370 nm. Observed peaks were scanned from 210-550 nm to obtain spectra. Chemstation software (Rev. A.8.03) was used to control the system and collect and analyse data.

Separation of flavonoid and isoflavonoid components within the extracts was performed using a gradient of acetonitrile in 1% acetic acid, at a flow rate of 0.8 ml/min. The gradient of acetonitrile was: 15-37% linear in 22 min, then 37-80% in 2 min, before a hold at 80% for 2 min. Then the acetonitrile was reduced from 80-15% in 2 min and held at 15% for 2 min prior to next injection.

Absorbance spectra (corrected for baseline spectrum) and retention time of peaks were compared with those of commercially available flavonoid and isoflavonoid standards.

Calibration curves for quercetin, kaempferol, genistein, daidzein, isoliquiritigenin and liquiritigenin were established to permit quantitation in the hydrolysed tobacco extracts. Levels were calculated on a fresh weight (μg/g F.wt.) basis. With the HPLC system and software used, detection limits in tobacco extracts was about 0.1 μg/ml, corresponding with ~1.5 μg/g fresh weight. Variation between replicate injections was less than 5%.

1.8.2 GC-MS Conditions for Flavonoid and Isoflavonoid Analysis

After hydrolysis, 5 ml of 10% $Na_2SO_4$ was added to an aliquot from each tissue extract before extraction with 2 ml ethyl acetate. The sample was then centrifuged at 1600 g for 1 min. The ethyl acetate layer was decanted to a fresh tube and evaporated to dryness under $N_2$ (<45° C.)

Samples were dissolved in 30 μl pyridine and derivatised by heating with 20 μl bis-trifluoroacetamide (BSTFA) at 45° C. for 15 min., 1 μl of sample was injected onto a CP-Sil 8 CB/MS (25 m×0.25 mm×0.25 μm film) GC capillary column (Chrompack) through a splitless injector port at 280° C. (Hewlett Packard 5890 gas chromatograph). The oven temperature was set at a linear temperature gradient from 100-320° C. at 10° C./min with a helium gas flow rate of 1 ml/min. The mass spectrum was monitored using a Hewlett Packard 5972A quadruple mass-selective detector set at 300° C. (EI) and mass ranges of 175, 184, 383, 398 Daltons for daidzein (selective ion mode); 228, 399, 371, 486 Daltons for genistein (selective ion mode); (219, 307, 371, 457 and 472 daltons for isoliquiritigenin (selective ion mode) and 151, 179, 192, 235, 385, and 400 daltons for liquiritigenin (selective ion mode). In addition, mass ranges of 170-400 Daltons for daidzein, 130-480 Daltons for isoliquiritigenin, 130-410 Daltons for liquiritigenin and 180-490 for genistein were selected for full scan mode.

1.9 Accumulation of Daidzein in Transgenic *N. tabacum* Ectopically Expressing Chalcone Reductase and Isoflavone Synthase:

To determine whether ectopic expression of both chalcone reductase and isoflavone synthase in the non-leguminous plant *N. tabacum* was able to redirect flavonoid synthesis toward daidzein and/or genistein synthesis, the flavonoid and isoflavonoid profile of petal tissues was determined. This analysis was performed by HPLC using hydrolysed extracts of petal tissue from nineteen pPE120 and six pPE51 transformants.

In the HPLC analysis comparison between hydrolysed petal extracts from flowers of *N. tabacum* transformed with either pPE120 or pPE51 indicated that in several of the pPE120 transformants a small peak with the same retention time as the daidzein standard was detected. By contrast, this HPLC peak was not present in control (pPE51) transformants. To confirm our preliminary identification, this peak was collected from the HPLC and analysed using GC-MS assay. In addition, fractions with the corresponding retention time were collected from a typical pPE51 transformant and from a daidzein standard as controls.

GC-MS analysis showed that the retention time and the relative abundance of the measured ions (175, 184, 383, and 398 [M+]) from the pPE120 fraction were similar to those from the authentic daidzein standard (FIG. 6). Furthermore, the fraction from pPE51 showed no GC peak with a similar retention time or with a similar relative abundance of the measured ions confirming the absence of daidzein in the control transformants (FIG. 6).

Quantitation, based on comparison with authentic standards showed that levels of daidzein accumulation in pPE120 petal tissues reached up to ~2.75 μg/gFwt (FIG. 7).

1.10 Daidzein Accumulation in Transgenic *N. tabacum* Expressing Chalcone Reductase, Isoflavone Synthase and Chalcone Isomerase.

To determine whether concomitant expression of chalcone reductase and isoflavone synthase in conjunction with a legume chalcone isomerase in the non-leguminous plant *N. tabacum* was able to enhance the level of daidzein accumulation, the flavonoid and isoflavonoid profile of petal tissues was determined. This analysis was performed by HPLC using hydrolysed extracts of petal tissue from twelve pPE125 and six pPE51 transformants.

In the HPLC assay comparison between hydrolysed petal extracts from flowers of *N. tabacum* transformed with either pPE125 or pPE51 indicated that for several of the pPE125 transformants a peak with the same retention time as the daidzein standard was detected. By contrast, this peak was not present in control (pPE51) transformants. To confirm our preliminary identification, the peak corresponding to daidzein was collected from the HPLC and analysed using GC-MS assay. In addition, fractions with the corresponding retention time were collected from a typical pPE51 transformant and from a daidzein standard as controls.

GC-MS analysis showed that the retention time and the relative abundance of the measured ions (175, 184, 383, and 398 [M+]) from the pPE125 fraction were similar to those from the authentic daidzein standard. Furthermore, the fraction from pPE51 showed no peak with a similar retention time or with a similar relative abundance of the measured ions confirming the absence of daidzein. Quantitation, based on comparison with authentic standards showed that levels of daidzein accumulation in pPE125 petal tissues reached up to 246.7 μg/gFwt (~4934 μg/gDwt) (FIG. 8).

EXAMPLE 2

Transformation of Lettuce

Stable Transformation of *Lactuca Sativa* L. cv Lollo Rossa, Bijou, Muscara & Revolution

*A. tumefaciens* cells from PCR positive colonies were used to inoculate a 10 ml Lennox media broth containing kanamycin 50 μg/ml and rifampicin 50 μg/ml and incubated overnight with shaking (120 rpm) at 29° C. The overnight culture was centrifuged at 3000 g and the cell pellet resuspended in an equal volume of UM media and a 1:10 (v/v) dilution used for transformation.

Cotyledons were cut from 7-day old *Lactuca Sativa* L. seedlings grown in tissue culture. The abaxial surface of the cotyledons was scored with a scalpel-blade before placing directly into the *A. tumefaciens* suspension and co-incubated for 10 minutes.

The cotyledons were then transferred, abaxial surface down, to solidified UM media supplemented with 3% (w/v) sucrose overlayed with one filter paper (8 per plate) and placed at 25° C. for 2 days. The cotyledons were then transferred, axial surface up, to solidified MS media supplemented with 3% (w/v) sucrose, 0.04 mgl$^{-1}$ NAA, 0.5 mgl$^{-1}$ BAP, 100 µg/ml cefotaxime, 500 µg/ml carbenicillin and 50 µg/ml kanamycin and placed in a growth room at 25° C. with a 16 hr photoperiod. The explants were transferred to fresh medium every 14 days. After eight weeks, regenerating explants were transferred to solidified MS media supplemented with 0.11% (w/v) MES, 100 µg/ml cefotaxime and 50 µg/ml kanamycin.

Genomic DNA was isolated from shoots that had rooted and transgenic plants harbouring the constructs were selected following specific amplification of the CHR, CHI & IFS transgenes respectively.

Transgene positive plants were then transferred to 9 cm diameter pots containing Levington M3 compost mixed with John Innes No. 3 & perlite (3:3:2) and placed in a propagator in a growthroom at 25° C. with a 16 hr photoperiod. After 1 week the plants were removed from the propagator and maintained at 25° C. with a 16 hr photoperiod.

Leaf tissue harvested from each independent transformant and is stored at −80° C. for subsequent flavonoid and isoflavonoid analyses as previously described.

EXAMPLE 3

Transformation of Potato

Stable Transformation of *Solanum tuberosum* L. cv. Desiree

*A. tumefaciens* cells from transgene positive (PCR) colonies were used to inoculate a 20 ml Lennox media broth containing kanamycin 50 µg/ml and rifampicin 50 µg/ml and incubated for 3-days with shaking (120 rpm) at 29° C. Following incubation, this culture was centrifuged at 3000 g and the cell pellet resuspended in 25 ml MS media (pH5.8) supplemented with 3% (w/v) sucrose.

Leaves were cut from 4-week old *Solanum tuberosum* L. plants, grown in tissue culture, and placed axial surface up onto solidified L3 medium [MS basal salts supplemented with 1.6% glucose, 0.8% agar, pH5.8] supplemented with 0.02 mg/l NAA, 20 mg/l GA$_3$, 2 mg/l Zeatin riboside] and placed at 23° C. for 2 days.

The excised leaves were then placed directly into the *A. tumefaciens* suspension and co-incubated for 10 minutes. Following co-incubation, the leaves were 'blotted-dry' and transferred, axial surface up, to feeder plates (solidified L3 media overlayed with 2 ml of tobacco cells suspension over which one filter paper was placed) and placed in darkness at 23° C. for 2 days. The leaf explants were then transferred, axial surface up, to solidified L3 media supplemented 0.02 mg/l NAA, 20 mg/l GA3, and 500 µg/ml cefotaxime and placed in a growth room at 23/C with a 16 hr photoperiod for four days. The leaf explants were then transferred to fresh L3 medium supplemented with 0.02 mg/l NAA, 20 mg/l GA3, and 500 µg/ml cefotaxime and 100 mg/l kanamycin every 14 days. After approximately eight weeks, shoots (~1.5 cm) were excised from the regenerating explants and transferred to solidified MS media supplemented with 1% (w/v) sucrose, 0.8% agar, 500 µg/ml cefotaxime and 100 µg/ml kanamycin.

Genomic DNA was isolated from shoots that had rooted and transgenic plants harbouring the constructs were selected following specific amplification of the CHR, CHI & IFS transgenes respectively.

Minitubers were initiated from each transgene positive plant by transfer of ~3 cm long leaf node to MS media supplemented with 8% (w/v) sucrose and 0.8% agar and maintaining in darkness at 25° C. Minitubers were harvested from each independent transformant and stored at −80° C. for subsequent flavonoid and isoflavonoid analyses.

EXAMPLE 4

Food Product: Skin Appearance Benefits from Isoflavone Consumption

The investigation was designed as a double blind placebo controlled study with 33 female post-menopausal volunteers. The participants were randomised in a parallel design into two groups to receive foods with and without functional ingredients for a period of 12 weeks in total. For the duration of the study the subjects had to avoid soya containing foods and stop taking vitamins, minerals or other dietary supplements.

The study comprised two phases. Firstly, a "run-in" or "washout" phase when subjects consumed placebo foods for two weeks. Secondly, an intervention phase when subjects were randomly allocated to consume foods (2 low-calorie food bars per day) containing functional ingredients or placebo foods for a further 10 weeks.

Study foods were provided as a low-calorie bar, The bars were small (serving size 29 g) and provided on average 108 calories and 3.1 g fat.

Each functional bar contained:

| | |
|---|---|
| Soya isoflavones | 20 mg |
| Green tea polyphenols | 100 mg |
| Gamma-linolenic acid | 240 mg |
| Carotenoids | 0.25 mg |
| Vitamin A | 300 µg |
| Vitamin C | 60 mg |
| Vitamin E | 7.5 mg |
| Vitamin B2 | 0.55 mg |
| Vitamin B3 | 7 mg |
| Vitamin B6 | 0.75 mg |
| Vitamin D | 5 µg |
| Folate | 200 µg |
| Zinc | 7.5 mg |
| Calcium | 600 mg |
| PABA | 120 mg |

The placebo foods contained the PABA (para-aminobenzoic acid) but none of the functional ingredients. PABA was added as a compliance marker to all the bars.

Consumption of the bars containing micronutrients of which the isoflavones are considered to most efficacious, resulted in a range of skin health and appearance benefits: i. Improved skin appearance and reduced signs of ageing due to reduced wrinkle height; ii. Improved firmness and skin tone; iii. Softer and smoother skin; iv. A less sensitive skin, that makes one feel better about their skin; v. Improved overall antioxidant status of the body and skin.

The statistical significance of each of the skin benefits or serum changes after ten weeks intervention is listed below:

| Parameter | Week 10 'p' value |
|---|---|
| i. Wrinkle height (replicas) | <0.078 |
| ii. Firmness (indent value) | <0.075 |
| iii. Softness/Smoothness (Coefficient of restitution) | <0.15 |
| iv. Sensitive skin (questionnaire) | <0.05 |
| v. Serum antioxidant status (TEAC) | <0.065 |

The invention claimed is:

1. A genetically modified plant or part thereof comprising daidzein and/or derivatives thereof, wherein said plant or part thereof does not naturally produce isoflavones and is active in both flavonol and anthocyanin biosynthesis and comprises:
   (a) a first nucleotide sequence encoding a chalcone reductase comprising an amino acid with at least 95% sequence identity to the amino acid sequence of SEQ ID NO: 2; and
   (b) a second nucleotide sequence encoding an isoflavone synthase comprising an amino acid sequence with at least 95% sequence identity to the amino acid sequence of SEQ ID NO: 4.

2. A genetically modified plant or part thereof according to claim 1, further comprising a third nucleotide sequence encoding a chalcone isomerase comprising an amino acid sequence with at least 95% sequence identity to the amino acid sequence of SEQ ID NO: 6.

3. A genetically modified plant or part thereof according to claim 1 wherein (i) the first nucleotide sequence comprises the nucleotide sequence of SEQ ID NO: 1, and (ii) the second nucleotide sequence comprises the nucleotide sequence of SEQ ID NO: 3.

4. A genetically modified plant or part thereof according to claim 2 wherein the third nucleotide comprises the nucleotide sequence of SEQ ID NO: 5.

5. A genetically modified plant or part thereof according claim 4 wherein the third nucleotide sequence consists of the nucleotide sequence as shown in SEQ ID NO: 5.

6. A genetically modified plant or part thereof according to claim 1 wherein said plant or part thereof is selected from the group consisting of tobacco, Lactuca sp., broccoli, asparagus, red cabbage, potato, spinach, rhubarb, red onion, shallot, aubergine, radish, Swiss chard, purple basil, watermelon and berries.

7. A food product comprising a genetically modified plant or part thereof according to claim 1.

8. A food product according to claim 7 wherein said food product is selected from the group consisting of packaged mixed salad, soup, spread, sauce, fruit bar and ice cream.

9. A method for the production of a food product or nutritional supplement comprising culturing the genetically modified plant or part thereof according to claim 1 under conditions suitable for expression of a chalcone reductase or isoflavone synthase.

10. A method for the production of a food product or nutritional supplement comprising culturing the genetically modified plant or part thereof according to claim 2 under conditions suitable for expression of a chalcone reductase or isoflavone synthase.

11. A process for increasing the content of daidzein and/or derivatives thereof in a plant or part thereof, wherein said process comprises:
   (i) selecting a non-isoflavone producing plant wherein said plant or part thereof is active in both anthocyanin and flavonol biosynthesis; and
   (ii) genetically modifying said plant to incorporate one or more nucleotide sequences encoding a chalcone reductase comprising an amino acid with at least 95% sequence identity to the amino acid sequence of SEQ ID NO: 2 with chalcone reductase activity and one or more nucleotide sequences encoding a isoflavone synthase comprising the an amino acid with at least 95% sequence identity to the amino acid sequence of SEQ ID NO: 4 with isoflavone synthase activity so as to increase the activity of chalcone reductase and isoflavone synthase in said plant or part thereof.

12. A process according to claim 11, wherein said process further comprises genetically modifying said plant or part thereof to incorporate one or more nucleotide sequences encoding a chalcone isomerase comprising an amino acid with at least 95% sequence identity to the amino acid sequence of SEQ ID NO: 6 capable of catalyzing the conversion of 4,2',4'-trihydroxchalcone to 7,4'-dihydroxyflavanone so as to increase the activity of the chalcone isomerase.

13. A process according to claim 11, wherein (i) one or more nucleotide sequences encoding a chalcone reductase comprises a nucleotide sequence as shown in SEQ ID NO: 1, and (ii) one or more nucleotide sequences encoding a isoflavone synthase comprises a nucleotide sequence as shown in SEQ ID NO: 3.

14. A process according to claim 12, wherein said one or more nucleotide sequences encoding a chalcone isomerase comprises a nucleotide sequence as shown in SEQ ID NO: 5.

15. A process according to claim 14, wherein said one or more nucleotide sequences encoding a chalcone isomerase consists of a nucleotide sequence as shown in SEQ ID NO: 5.

16. A process according to claim 11 wherein said plant is selected from the group consisting of tobacco, Lactuca sp., broccoli, asparagus, red cabbage, potato, spinach, rhubarb, red onion, shallot, aubergine, radish, Swiss chard, purple basil, watermelon and berries.

17. A genetically modified plant or part thereof according to claim 1, wherein the first nucleotide sequence encodes a chalcone reductase comprising the amino acid sequence of SEQ ID NO: 2.

18. A genetically modified plant or part thereof according to claim 1, wherein the first nucleotide sequence encodes a chalcone reductase consisting of the amino acid sequence of SEQ ID NO: 2.

19. A genetically modified plant or part thereof according to claim 1, wherein the second nucleotide sequence encodes a isoflavone synthase comprising the amino acid sequence of SEQ ID NO: 4.

20. A genetically modified plant or part thereof according to claim 1, wherein the second nucleotide sequence encodes a isoflavone synthase consisting of the amino acid sequence of SEQ ID NO: 4.

21. A genetically modified plant or part thereof according to claim 2, wherein the third nucleotide sequence encodes a chalcone isomerase comprising the amino acid sequence of SEQ ID NO: 6.

22. A genetically modified plant or part thereof according to claim 3, wherein the first nucleotide sequence consists of the nucleotide sequence of SEQ ID NO: 1.

23. A genetically modified plant or part thereof according to claim 3, wherein the second nucleotide sequence consists of the nucleotide sequence of SEQ ID NO: 3.

24. The process of claim 11, wherein the chalcone reductase comprises the amino acid sequence of SEQ ID NO: 2.

25. The process of claim 11, wherein the chalcone reductase consists of the amino acid sequence of SEQ ID NO: 2.

26. The process of claim 11, wherein the isoflavone synthase comprises the amino acid sequence of SEQ ID NO: 4.

27. The process of claim 11, wherein the isoflavone synthase consists of the amino acid sequence of SEQ ID NO: 4.

28. The process of claim 12, wherein the chalcone isomerase comprises the amino acid sequence of SEQ ID NO: 6.

29. The process of claim 12, wherein the nucleotide sequence encoding the chalcone isomerase consists of the amino acid sequence of SEQ ID NO: 6.

30. The process of claim 13, wherein the nucleotide sequence encoding the chalcone reductase consists of the nucleotide sequence of SEQ ID NO: 1.

31. The process of claim 13, wherein the nucleotide sequence encoding the isoflavone synthase consists of the nucleotide sequence of SEQ ID NO: 3.

* * * * *

SEQUENCE LISTING

<160> NUMBER OF SEQ ID NOS: 59

<210> SEQ ID NO 1
<211> LENGTH: 946
<212> TYPE: DNA
<213> ORGANISM: Pisum sativum

<400> SEQUENCE: 1

```
atgggtagtg ttgaaatccc aacaaaggtg cttaccaaca catctgctca aattaagatg      60
cctgttgttg gaatgggatc agcacctgac ttcacatgca agaaagacac taaagaagca     120
atcatcgaag ccatcaaaca aggttacaga cactttgata ctgctgctgc ttatggatcc     180
gaacaagctc ttggtgaggc tttgaatgag ctattcaac ttggtcttgt cactagagaa      240
cagcttttg ttacttctaa actttgggtt actgaaaatc atcctcacct tgttcttcct      300
gctctacaaa aatctctcaa gactcttcag ttggattact ggatttgta tttgattcat      360
tggccactta gttctcagcc cggaaagttt tcatttccaa ttgatgtggc tgatctattg     420
ccatttgatg taaaggtgt gtgggaatcc atggaagagg ctttgagact tggactcacg      480
aaagctattg gtgtcagtaa cttctctgtc aagaaacttc aaaagctact atctgttgcc     540
actgttcttc ctgctgttaa tcaagtagag atgaaccttg catggcaaca aaagaagcta     600
agagaattt gcaatgaaaa tggaatagtg ttgactgcat tttcaccgtt gaggaaaggc      660
gccagccgag gagcaaatga ggttatggag aatgatatgc ttaaacagat tgcagatgct     720
catggaaagt ctattgcaca aatttctctg agatggttat atgaacaagg aatcactttt      780
gttccaaaga gctatgataa ggagagaatg agtcaaaatt tgagaatctt tgattggaca     840
ctgacaaagg aggatcatga gaaaattgat caaattaagc agaatcgttt gatccctgga     900
ccaaccaagc caagtctcaa tgatctttgg gatgatgaaa tataag                    946
```

<210> SEQ ID NO 2
<211> LENGTH: 314
<212> TYPE: PRT
<213> ORGANISM: Pisum sativum

<400> SEQUENCE: 2

```
Met Gly Ser Val Glu Ile Pro Thr Lys Val Leu Thr Asn Thr Ser Ala
1               5                   10                  15

Gln Ile Lys Met Pro Val Val Gly Met Gly Ser Ala Pro Asp Phe Thr
            20                  25                  30

Cys Lys Lys Asp Thr Lys Glu Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Asn Glu Ala Ile Gln Leu Gly Leu Val Thr Arg Glu
65                  70                  75                  80
```

```
Gln Leu Phe Val Thr Ser Lys Leu Trp Val Thr Glu Asn His Pro His
                 85                  90                  95
Leu Val Leu Pro Ala Leu Gln Lys Ser Leu Lys Thr Leu Gln Leu Asp
            100                 105                 110
Tyr Leu Asp Leu Tyr Leu Ile His Trp Pro Leu Ser Ser Gln Pro Gly
        115                 120                 125
Lys Phe Ser Phe Pro Ile Asp Val Ala Asp Leu Leu Pro Phe Asp Val
    130                 135                 140
Lys Gly Val Trp Glu Ser Met Glu Glu Ala Leu Arg Leu Gly Leu Thr
145                 150                 155                 160
Lys Ala Ile Gly Val Ser Asn Phe Ser Val Lys Leu Gln Lys Leu
                165                 170                 175
Leu Ser Val Ala Thr Val Leu Pro Ala Val Asn Gln Val Glu Met Asn
            180                 185                 190
Leu Ala Trp Gln Gln Lys Lys Leu Arg Glu Phe Cys Asn Glu Asn Gly
        195                 200                 205
Ile Val Leu Thr Ala Phe Ser Pro Leu Arg Lys Gly Ala Ser Arg Gly
    210                 215                 220
Ala Asn Glu Val Met Glu Asn Asp Met Leu Lys Gln Ile Ala Asp Ala
225                 230                 235                 240
His Gly Lys Ser Ile Ala Gln Ile Ser Leu Arg Trp Leu Tyr Glu Gln
                245                 250                 255
Gly Ile Thr Phe Val Pro Lys Ser Tyr Asp Lys Glu Arg Met Ser Gln
            260                 265                 270
Asn Leu Arg Ile Phe Asp Trp Thr Leu Thr Lys Glu Asp His Glu Lys
        275                 280                 285
Ile Asp Gln Ile Lys Gln Asn Arg Leu Ile Pro Gly Pro Thr Lys Pro
    290                 295                 300
Ser Leu Asn Asp Leu Trp Asp Asp Glu Ile
305                 310

<210> SEQ ID NO 3
<211> LENGTH: 1567
<212> TYPE: DNA
<213> ORGANISM: Glycine max

<400> SEQUENCE: 3
atggtgcttg aacttgcact tggtttattg gttttggctc tgtttctgca cttgcgtccc       60
acacccactg caaaatcaaa agcacttcgc catctcccaa acccaccaag cccaaagcct      120
cgtcttccct tcataggaca ccttcatctc ttaaaagaca aacttctcca ctacgcactc      180
atcgacctct ccaaaaaaca tggtccctta ttctctctct actttggctc catgccaacc      240
gttgttgcct ccacaccaga attgttcaag ctcttcctcc aaacgcacga ggcaacttcc      300
ttcaacacaa ggttccaaac ctcagccata gacgcctca cctatgatag ctcagtggca      360
atggttccct tcgggcccta ctggaagttc gtgaggaagc tcatcatgaa cgaccttctc      420
aacgccacca ctgtaaacaa gttgaggcct tgaggaccc aacagacgcg taagttcctt      480
agggttatgg cccaaggcgc agaggcacag aagccccttg acttgaccga ggagcttctg      540
aaatggacca acagcaccat ctccatgatg atgctcggcg aggctgagga gatcagagac      600
atcgctcgcg aggttcttaa gatctttggc gaatacagcc tcactgactt catctggcca      660
ttgaagcatc tcaaggttgg aaagtatgag aagaggatcg acgacatctt gaacaagttc      720
gaccctgtcg ttgaaagggt catcaagaag cgccgtgaga tcgtgaggag gagaaagaac      780
```

```
ggagaggttg ttgagggtga ggtcagcggg gttttccttg acactttgct cgagttcgct      840
gaggatgaga ctatggagat caaaatcacc aaggaccaca tcaagggtct tgttgtagac      900
tttttctcgg caggaacaga ctcaacagcg gtggcaacag agtgggcatt ggcagaactc      960
atcaacaatc ctaaggtgtt ggaaaaggct cgtgaggagg tctacagtgt tgtgggaaag     1020
gacagacttg tggacgaagt tgacactcaa aaccttcctt acattagagc aatcgtgaag     1080
gagacattcc gcatgcaccc gccactccca gtggtcaaaa gaaagtgcac agaagagtgt     1140
gagattaatg gatatgtgat cccagaggga gcattgattc tcttcaatgt atggcaagta     1200
ggaagagacc ccaaatactg ggacagacca tcggagttcc gtcctgagag gttcctagag     1260
acagggctg aagggaagc agggcctctt gatcttaggg gacaacattt tcaacttctc       1320
ccatttgggt ctgggaggag aatgtgccct ggagtcaatc tggctacttc gggaatggca     1380
acacttcttg catctcttat tcagtgcttc gacttgcaag tgctgggtcc acaaggacag     1440
atattgaagg gtggtgacgc caaagttagc atggaagaga gagccggcct cactgttcca     1500
agggcacata gtcttgtctg tgttccactt gcaaggatcg gcgttgcatc taaactcctt     1560
tcttaag                                                               1567

<210> SEQ ID NO 4
<211> LENGTH: 521
<212> TYPE: PRT
<213> ORGANISM: Glycine max

<400> SEQUENCE: 4

Met Val Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
        115                 120                 125

Lys Phe Val Arg Lys Leu Ile Met Asn Asp Leu Leu Asn Ala Thr Thr
    130                 135                 140

Val Asn Lys Leu Arg Pro Leu Arg Thr Gln Gln Thr Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys His Leu
    210                 215                 220

Lys Val Gly Lys Tyr Glu Lys Arg Ile Asp Asp Ile Leu Asn Lys Phe
```

```
                  225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Val Ser Gly Val Phe
            260                 265                 270

Leu Asp Thr Leu Leu Glu Phe Ala Glu Asp Glu Thr Met Glu Ile Lys
        275                 280                 285

Ile Thr Lys Asp His Ile Lys Gly Leu Val Val Asp Phe Phe Ser Ala
    290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Thr Glu Glu Cys Glu Ile Asn Gly
    370                 375                 380

Tyr Val Ile Pro Glu Gly Ala Leu Ile Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Gly Pro Leu Asp Leu
            420                 425                 430

Arg Gly Gln His Phe Gln Leu Leu Pro Phe Gly Ser Gly Arg Arg Met
        435                 440                 445

Cys Pro Gly Val Asn Leu Ala Thr Ser Gly Met Ala Thr Leu Leu Ala
    450                 455                 460

Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
        515                 520

<210> SEQ ID NO 5
<211> LENGTH: 670
<212> TYPE: DNA
<213> ORGANISM: Lotus corniculatus

<400> SEQUENCE: 5
atggctgcat ccctcacccc aatccaggtc gagaaccttc aatttcctgc gtctgtcacc      60
tctccagcca ccgccaagtc ttatttcctc ggtggtgcag ggagagagg gttgacgatt     120 gaggggaagt tcataaaatt cactggcata ggagtgtatt ggaagatac agcagtggat     180 tcactcgcca ccaagtggaa gggtaagagt tcacaagagc tgcaggactc ccttgacttc     240
ttcagagaca tcatttcaag tccctctgag aagttaattc gagggtccaa gctgaggcca     300
ttgagtggcg tggagtattc aagaaaggtg atggagaatt gtgtggcaca catgaagtct     360
gctggaactt atggtgaagc agaggccaca gccattgaaa aatttgcaga agccttcagg     420
aaggtggatt ttccaccagg ttcctctgtt ttctaccgac aatcaacaga tggaaaatta     480
```

```
gggcttagtt tctctttgga tgacacgata ccagaagaag aggctgtagt tatagagaac    540
aaggcactct cagaggcagt gttagagacc atgattggcg agcatgctgt tcccctgat    600 ttgaagcgtt gtttggctga aaggttgcct attgtgatga accagggtct tctcctcact    660
ggaaactgat                                                          670
```

```
<210> SEQ ID NO 6
<211> LENGTH: 222
<212> TYPE: PRT
<213> ORGANISM: Lotus corniculatus

<400> SEQUENCE: 6
```

Met Ala Ala Ser Leu Thr Pro Ile Gln Val Glu Asn Leu Gln Phe Pro
1               5                   10                  15

Ala Ser Val Thr Ser Pro Ala Thr Ala Lys Ser Tyr Phe Leu Gly Gly
            20                  25                  30

Ala Gly Glu Arg Gly Leu Thr Ile Glu Gly Lys Phe Ile Lys Phe Thr
        35                  40                  45

Gly Ile Gly Val Tyr Leu Glu Asp Thr Ala Val Asp Ser Leu Ala Thr
    50                  55                  60

Lys Trp Lys Gly Lys Ser Ser Gln Glu Leu Gln Asp Ser Leu Asp Phe
65                  70                  75                  80

Phe Arg Asp Ile Ile Ser Ser Pro Ser Glu Lys Leu Ile Arg Gly Ser
                85                  90                  95

Lys Leu Arg Pro Leu Ser Gly Val Glu Tyr Ser Arg Lys Val Met Glu
            100                 105                 110

Asn Cys Val Ala His Met Lys Ser Ala Gly Thr Tyr Gly Glu Ala Glu
        115                 120                 125

Ala Thr Ala Ile Glu Lys Phe Ala Glu Ala Phe Arg Lys Val Asp Phe
    130                 135                 140

Pro Pro Gly Ser Ser Val Phe Tyr Arg Gln Ser Thr Asp Gly Lys Leu
145                 150                 155                 160

Gly Leu Ser Phe Ser Leu Asp Asp Thr Ile Pro Glu Glu Glu Ala Val
                165                 170                 175

Val Ile Glu Asn Lys Ala Leu Ser Glu Ala Val Leu Glu Thr Met Ile
            180                 185                 190

Gly Glu His Ala Val Ser Pro Asp Leu Lys Arg Cys Leu Ala Glu Arg
        195                 200                 205

Leu Pro Ile Val Met Asn Gln Gly Leu Leu Leu Thr Gly Asn
    210                 215                 220

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:conserved
      regions of various known CHR's

<400> SEQUENCE: 7
```

Met Pro Val Val Gly Met Gly Ser Ala
1               5

```
<210> SEQ ID NO 8
<211> LENGTH: 8
<212> TYPE: PRT
<213> ORGANISM: Artificial Sequence
<220> FEATURE:
```

```
<223> OTHER INFORMATION: Description of Artificial Sequence:conserved
      regions of various known CHR's

<400> SEQUENCE: 8

Ala Ile Ile Glu Ala Ile Lys Gln
1               5

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 9
atgttgctgg aacttgcact t                                              21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 10
ttagaaagga gtttagatgc aacg                                           24

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 11
tgtttctgca ttgcgtccca c                                              21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 12
ccgatccttg caagtggaac ac                                             22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 13
ttgtccagat agcccagtag ctg                                            23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 14
cgacaatctg atcatgagcg gag                                            23
```

```
<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 15
cgacaatctg atcatgagcg gag                                         23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 16
gcatcacgca gttcaacgct g                                           21

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 17
ggaaacagct atgaccatga ttac                                        24

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 18
aaggatccgt cgacatc                                                17

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 19
agtcccccat ggtacgtcct gtagaaacc                                   29

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 20
cgttttcgtc ggtaatcacc attcc                                       25

<210> SEQ ID NO 21
<211> LENGTH: 20
<212> TYPE: DNA
<213> ORGANISM: Artificial Sequence
<220> FEATURE:
```

<223> OTHER INFORMATION: Description of Artificial Sequence:primer

<400> SEQUENCE: 21
tttcccagtc acgacgttgt                                        20

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 22
gacatcgata atacgac                                           17

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 23
tgctacctct agagaatttc cccg                                   24

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 24
ctaagcccct aagtattcca tcaggtgatt                             30

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 25
ccaggtggaa aattacacat gtgcttgaaa gagc                        34

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 26
tttgaaaagt ctaataacga gggtcagaag                             30

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 27
tactcaagga aggttgatgg agaactgtcg tgg                         33

```
<210> SEQ ID NO 28
<211> LENGTH: 64
<212> TYPE: DNA
<213> ORGANISM: Artificial Sequence
<220> FEATURE:
<223> OTHER INFORMATION: Description of Artificial Sequence:primer

<400> SEQUENCE: 28
cgcgagctca tgtaccccgg gatttccact agtttaaggg ttaactacat ggtcgacgta      60
cata                                                                  64

<210> SEQ ID NO 29
<211> LENGTH: 70
<212> TYPE: DNA
<213> ORGANISM: Artificial Sequence
<220> FEATURE:
<223> OTHER INFORMATION: Description of Artificial Sequence:primer

<400> SEQUENCE: 29
agcttatgta cgtcgaccat gtagttaacc cttaaactag tggaaatccc ggggtacatg      60
agctcgcgat                                                            70

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence:primer

<400> SEQUENCE: 30
aattcgagct catgtacccc gggatttcca ctagtttaag ggttaactac atggtcgacg      60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence:primer

<400> SEQUENCE: 31
ctagcgtcga ccatgtagtt aacccttaaa ctagtggaaa tcccggggta catgagctcg      60

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 32
catggatgcg tagttaagcc t                                               21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 33
ctagaggctt acatacgcat c                                               21

<210> SEQ ID NO 34
<211> LENGTH: 72
<212> TYPE: DNA
```

<213> ORGANISM: Artificial Sequence
<220> FEATURE:
<223> OTHER INFORMATION: Description of Artificial Sequence:primer

<400> SEQUENCE: 34
aattcatgta cgagctcaat tcccccggga taggcactag tgctgctgtt aactacatgg    60
tcgacttatt aa                                                       72

<210> SEQ ID NO 35
<211> LENGTH: 72
<212> TYPE: DNA
<213> ORGANISM: Artificial Sequence
<220> FEATURE:
<223> OTHER INFORMATION: Description of Artificial Sequence:primer

<400> SEQUENCE: 35
aggtttaata agtcgaccat gtagttaaca gcagcactag tgcctatccc ggggaattg    60 agctcgtaca tg                                                       72

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 36
gaacaccatg gtgcttgaac ttgc                                          24

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 37
tccagtaggg cccgaaggga accattgcca c                                  31

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 38
ccttcgggcc ctactggaag                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 39
cagcgaactc gagcaaagtg                                               20

<210> SEQ ID NO 40
<211> LENGTH: 79
<212> TYPE: DNA
<213> ORGANISM: Artificial Sequence
<220> FEATURE:
<223> OTHER INFORMATION: Description of Artificial Sequence:primer

```
<400> SEQUENCE: 40
cactttgctc gagttcgctg aggatgagac tatggagatc aaaatcacca aggaccacat      60
caagggtctt gttgtagac                                                   79

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 41
atgacgagct agcttattaa gaaaggag                                         28

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 42
ggtgtgtggg gatccatgga agaggctttg                                       30

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 43
cctcggctcg cgcctttcct caacggtgaa aatgcagtca acac                       44

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 44
caacaaccca tgggtagtgt tgaaatccca acaaggtgc ttacc                       45

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 45
agcaactgct agcttatatt tcatcatccc aaagatc                               37

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 46
tagattgcca tggctgcatc cctcacccca atccaggtcg ag                         42
```

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 47
aaactttgct agcttatcag tttccagtga ggagaagac        39

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 48
gcttgttcgg atccataagc agc        23

<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 49
tgcttatgga tccgaacaag ctcttggtga ggctttgaat g        41

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 50
cagccacatc aattggaaat g        21

<210> SEQ ID NO 51
<211> LENGTH: 78
<212> TYPE: DNA
<213> ORGANISM: Artificial Sequence
<220> FEATURE:
<223> OTHER INFORMATION: Description of Artificial Sequence:primer

<400> SEQUENCE: 51
tcatttccaa ttgatgtggc tgatctattg ccatttgatg taaaaggtgt gtgggaatcc        60
atggaagagg ctttgaga        78

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 52
cacaagagct gcaggactcc cttga        25

<210> SEQ ID NO 53
<211> LENGTH: 24
<212> TYPE: DNA
<213> ORGANISM: Artificial Sequence

```
<220> FEATURE:
<223> OTHER INFORMATION: Description of Artificial Sequence:primer

<400> SEQUENCE: 53
gggagtcctg cagctcttgt gaac                                              24

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 54
agctgcgatc gcaagcttgg taccgggaat tctctaga                               38

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 55
aatttctaga gaattcccgg taccaagctt gcttgcgatc gc                          42

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 56
tcgacccatg gcccgctagc caattggagc t                                      31

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 57
ccaattggct agcgggccat ggg                                               23

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 58
ccacccacga gggaacatcg tg                                                22

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 59
gaattcccat ggtttacact cgaggtcctc tccaaatga                              39
```